(12) United States Patent
Tocci et al.

(10) Patent No.: US 7,177,085 B2
(45) Date of Patent: Feb. 13, 2007

(54) MULTIPLE IMAGING SYSTEM AND METHOD FOR DESIGNING SAME

(75) Inventors: Michael D. Tocci, Sandia Park, NM (US); Nora C. Tocci, Sandia Park, NM (US); Gregory C. Mooradian, San Diego, CA (US)

(73) Assignee: Science & Engineering Associates, Inc., Albuquerque, NM (US)

( * ) Notice: Subject to any disclaimer, the term of this patent is extended or adjusted under 35 U.S.C. 154(b) by 294 days.

(21) Appl. No.: 10/387,851

(22) Filed: Mar. 13, 2003

(65) Prior Publication Data

US 2003/0173503 A1    Sep. 18, 2003

Related U.S. Application Data

(60) Provisional application No. 60/363,997, filed on Mar. 14, 2002.

(51) Int. Cl.
*G02B 27/30* (2006.01)
(52) U.S. Cl. ........................................ 359/639; 359/738
(58) Field of Classification Search ................ 359/618, 359/639, 640, 732–740, 754–756, 763, 771, 359/784, 793; 356/320
See application file for complete search history.

(56) References Cited

U.S. PATENT DOCUMENTS

| 3,726,596 | A | * | 4/1973 | Triller et al. | 356/213 |
| 3,900,263 | A | * | 8/1975 | Hall, Jr. | 356/300 |
| 4,329,024 | A | * | 5/1982 | Rogers | 359/733 |

(Continued)

FOREIGN PATENT DOCUMENTS

EP    0403467 A2    12/1990

(Continued)

OTHER PUBLICATIONS

U.S. Appl. No. 60/363,997, filed Mar. 14, 2002, "Multiple Imaging System and Method for Designing Same." Applicats: Michael D. Tocci et al.

(Continued)

*Primary Examiner*—Hung X. Dang
*Assistant Examiner*—Joseph Martinez
(74) *Attorney, Agent, or Firm*—Burns & Levinson LLP; Jacob N. Erlich; Orlando Lopez

(57) ABSTRACT

An optical system of the present invention produces multiple simultaneous adjoining images on a single image plane. The optical system includes a first optical sub-system, a second optical sub-system, an aperture stop located between the first optical sub-system and the second optical sub-system, and a beam separating sub-system located at a plane substantially coincident with the aperture stop. The beam separating sub-system can receive electromagnetic radiation from the first optical sub-system and can separate the received electromagnetic radiation into multiple beams of electromagnetic radiation. The second optical sub-system images the multiple beams of electromagnetic radiation received from the beam separating sub-system into multiple images on an image plane. The beam separating sub-system includes one or more beam separating components and a mid-system filter system. An output filter, overlaid on the imaging plane, prevents light from any one of the images from passing through to the portion of the image plane corresponding to any one of the other images.

34 Claims, 31 Drawing Sheets

U.S. PATENT DOCUMENTS

| | | |
|---|---|---|
| 4,933,751 A | 6/1990 | Shinonaga et al. ............ 358/55 |
| 5,024,530 A | 6/1991 | Mende ........................ 356/402 |
| 5,194,959 A | 3/1993 | Kaneko et al. .............. 358/225 |
| 5,317,450 A * | 5/1994 | Kamon ........................ 359/566 |
| 5,548,444 A * | 8/1996 | McLaughlin et al. ........ 359/629 |
| 5,642,191 A | 6/1997 | Mende ........................ 356/326 |
| 5,729,011 A * | 3/1998 | Sekiguchi ................... 250/226 |
| 5,926,283 A * | 7/1999 | Hopkins ..................... 356/419 |
| 2002/0007123 A1 | 1/2002 | Balas .......................... 600/476 |
| 2002/0054428 A1 * | 5/2002 | Seward ....................... 359/362 |

FOREIGN PATENT DOCUMENTS

| | | |
|---|---|---|
| GB | 656908 | 9/1951 |
| GB | 2338080 A | 12/1999 |

OTHER PUBLICATIONS

European Examination Report, European Application No. 03714149.6 for Science & Engineering Associates, Inc., Feb. 11, 2005.

* cited by examiner

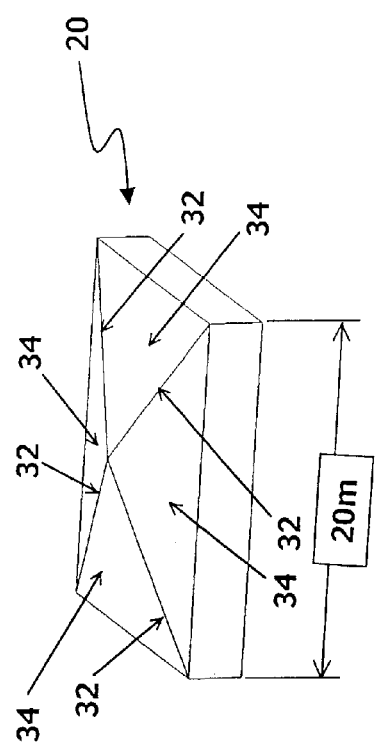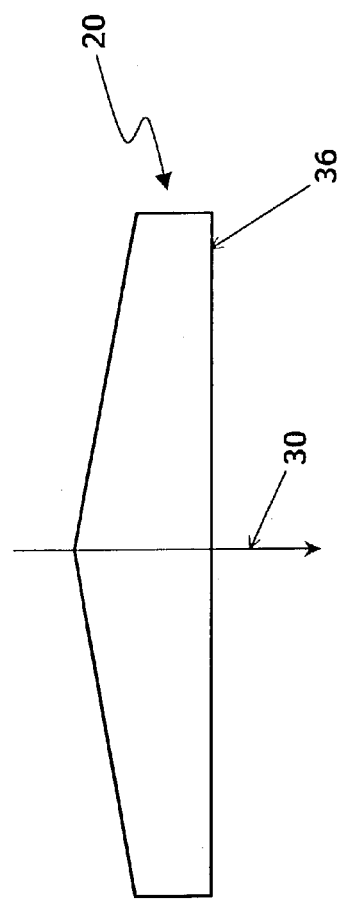

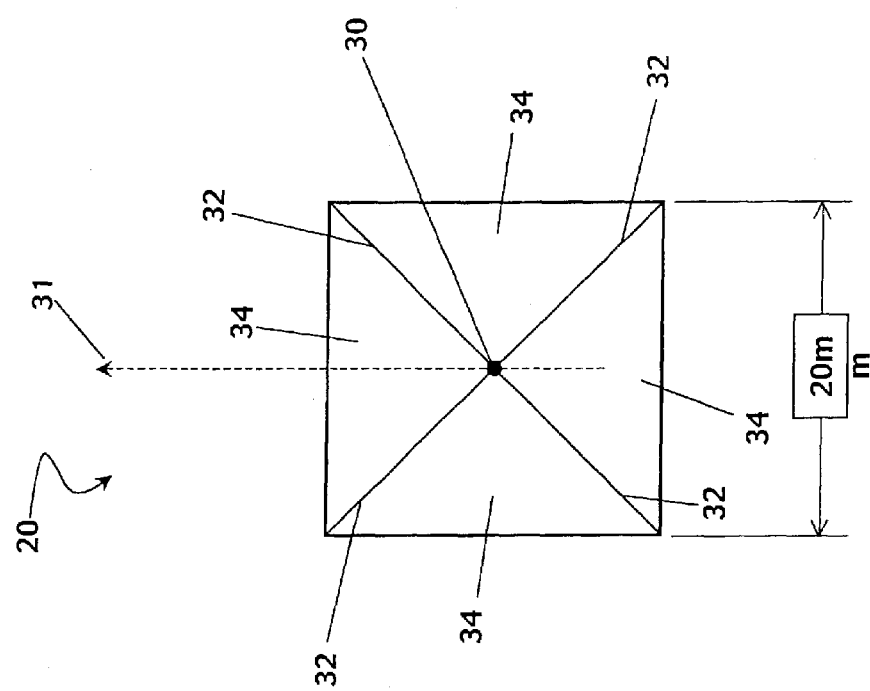

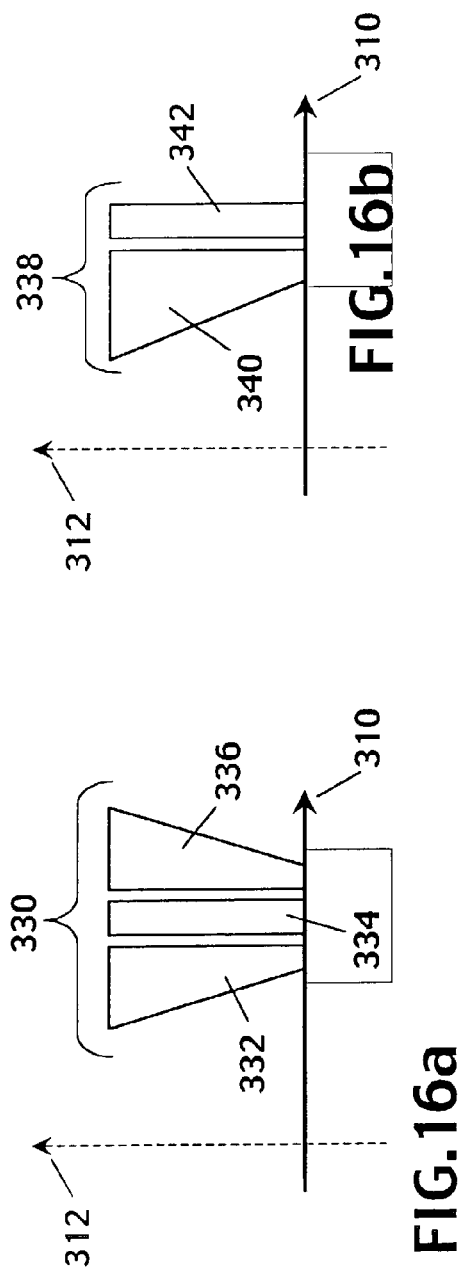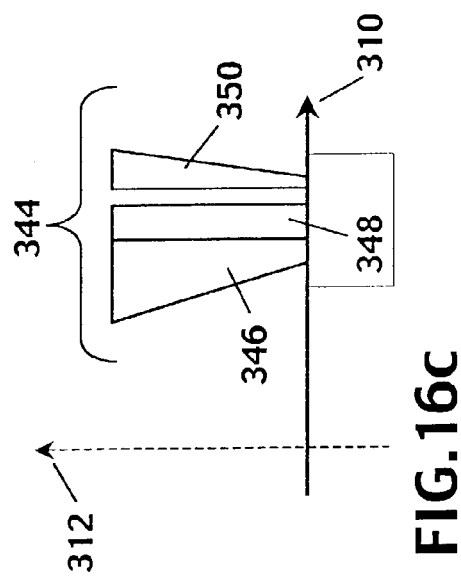

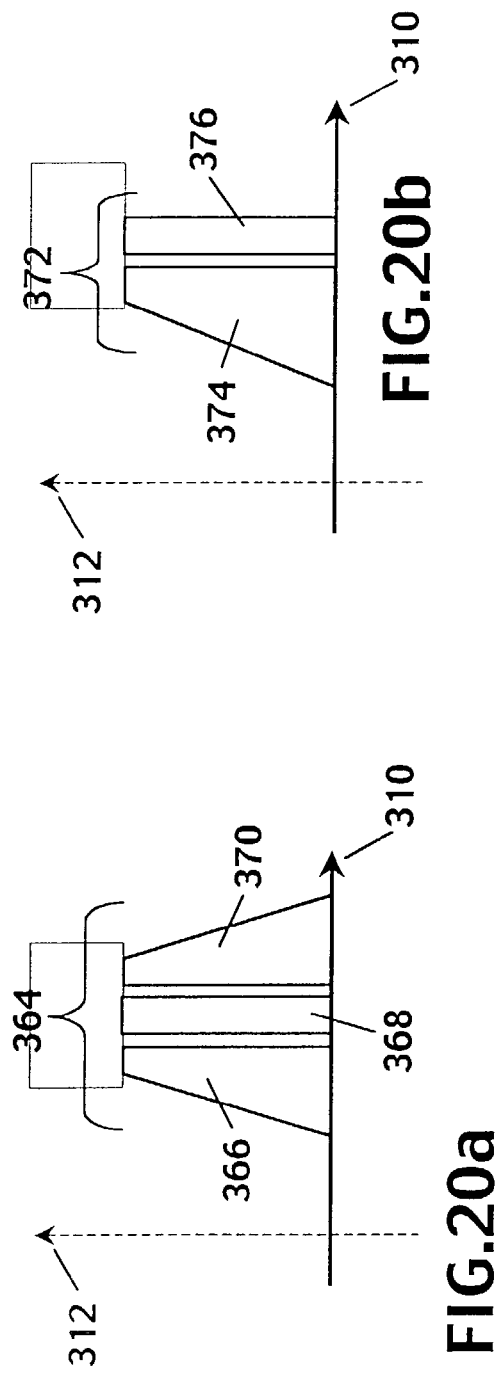
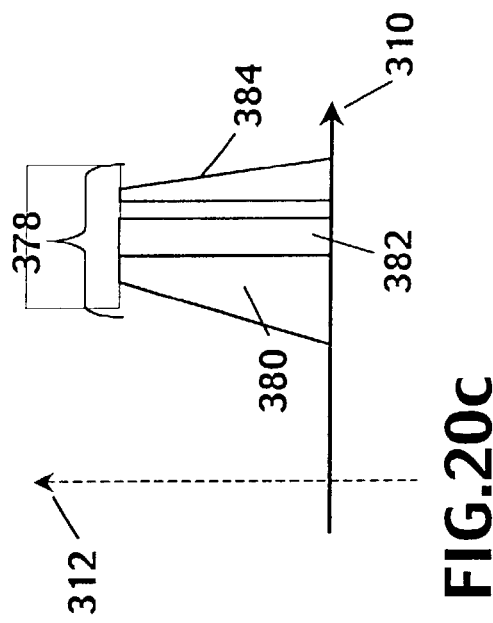
FIG.20a
FIG.20b
FIG.20c

MULTIPLE IMAGING SYSTEM AND METHOD FOR DESIGNING SAME

CROSS REFERENCE TO RELATED APPLICATIONS

This application claims priority of U.S. Provisional Application No. 60/363,997 filed on Mar. 14, 2002, which is incorporated by reference herein.

BACKGROUND OF THE INVENTION

This invention relates generally to imaging systems and more particularly to an imaging system that produces multiple images of a single object scene onto a single detector array. These multiple images are spatially displaced from one another on a single detector array in the image plane.

In some specialized applications, such as long-range multi-spectral imaging, there is a great desire to produce several images of a given object scene simultaneously on a single detector array (such as a CCD). For applications such as multi-spectral imaging, each of these separate images is passed through a different colored filter. Presently, multi-spectral imaging is typically performed either with rotating filter wheels (which are unable to record more than a single image simultaneously) or with a plurality of imaging and detection systems (which inherently are unable to image onto a single detector array).

Multi-spectral systems that rely on rotating filter wheels produce images through various filters, one-at-a-time, and in succession. In cases where it is important to produce differently-filtered images simultaneously, filter-wheel-dependent multi-spectral systems are inadequate.

U.S. Pat. No. 5,194,959 describes a multi-spectral imaging system that produces differently-filtered images simultaneously on three different imaging sensors. One major drawback with this system is that three imaging sensors, which can often be quite expensive, are required. In addition, in cases where high-performance and/or low-contrast imaging is to be performed, it is desirable to compare images formed on a single imaging sensor. The reason for this is that every imaging sensor, no matter how similar, is different in some way than every other imaging sensor, especially through a large range of illumination levels. For example, something as simple as a slight difference in temperature stability between two imaging sensors can make very fine comparisons of images made on the two imaging sensors practically impossible. For many multi-spectral applications, it is absolutely necessary to produce multiple images on a single imaging sensor.

U.S. Pat. Nos. 4,933,751, 5,024,530, 5,642,191, 5,729,011, and 5,926,283 each describe an apparatus and/or method for producing multiple images simultaneously on a single imaging sensor. All of these prior art patents have shortcomings, which are directly addressed in the invention described herein.

U.S. Pat. Nos. 4,933,751 and 5,926,283 describe apparatuses that require mirror reflection of the optical beam in "off-axis" or "perpendicular" directions. Because of the convoluted orientation of the multiple off-axis mirrors in these designs, complex positioning systems are required.

U.S. Pat. No. 5,729,011 describes an apparatus that positions the image-separating prism at a point in the optical train where the light is converging. Whereas positioning of the prism at a point in the optical train where light is collimated would produce sharp, well-resolved images, positioning of the prism at a point in the optical train where light is converging introduces a number of aberrations and degrades image quality. Therefore an apparatus that positions the prism at a point in the optical train where light is converging is inferior to one that takes care to position the prism in a collimated-light space.

U.S. Pat. Nos. 5,642,191 and 5,024,530 describe apparatuses in which splitting of the image into only two images is anticipated, and means are not shown for the more complex case where four or more images are to be produced. Furthermore, these patents require several imaging lens systems in order to create a first image, collimate the light, and then to form a second image. These multiple imaging lens systems more costly, larger, and cause more imaging aberrations than the single imaging lens system described in the present invention.

It is therefore an object of this invention to produce multiple images of the same object scene simultaneously and adjoining one another on a single detector plane.

It is another object of this invention to effect such imaging with an optical system that exhibits no vignetting (obscuration of a portion of the light reaching the detector).

It is another object of this invention to effect such imaging with an optical system that requires no off-axis optical elements.

It is another object of this invention to effect such imaging with a single optical imaging lens system.

It is another object of this invention to effect such imaging without the need for mirrors.

SUMMARY OF THE INVENTION

The objects set forth above as well as further and other objects and advantages of the present invention are accomplished by the embodiments of the invention described herein below.

The present invention uses a series of optical elements (an optical system) to produce multiple simultaneous adjoining images on a single image plane. A beam separating subsystem of this invention is located at a plane substantially coincident with the aperture stop of a color-corrected imaging lens. The image produced by this optical system consists of a plurality of identical images of the object, wherein each of these images may be composed of a different component, or set of components, of the original incident light. A filter of this invention, overlaid on the imaging plane, prevents light from any one of the images from passing through to the portion of the imaging plane corresponding to any one of the other images.

For a better understanding of the present invention, together with other and further objects thereof, reference is made to the accompanying drawings and detailed description.

BRIEF DESCRIPTION OF THE DRAWINGS

FIG. 2a is a schematic illustration of a first preferred embodiment of the first prism;

FIG. 2b is a schematic side-view illustration of a first preferred embodiment of the first prism;

FIG. 2c is a schematic front-view illustration of a first preferred embodiment of the first prism;

FIG. 16a is a schematic illustration of a form for the filter and prism group;

FIG. 16b is a schematic illustration of another form for the filter and prism group;

FIG. 16c is a schematic illustration of yet another form for the filter and prism group;

FIG. 20a is a schematic illustration of yet another form for the filter and prism group;

FIG. 20b is a schematic illustration of yet another form for the filter and prism group;

FIG. 20c is a schematic illustration of yet another form for the filter and prism group;

DETAILED DESCRIPTION OF THE PREFERRED EMBODIMENT

In the following descriptions of the present invention, the terms "light", "optical radiation" and "electromagnetic radiation" may be used interchangeably, and these terms both include, but are not limited to, for example, ultraviolet, visible, and infrared electromagnetic radiation with wavelength(s) in the range from 0.2 micron to 20 microns. Similarly, the term "optical system", as used herein, includes systems to operate on "electromagnetic radiation", wherein such operations include, but are not limited to, directing, receiving, or filtering "electromagnetic radiation". The term "color corrected", as used herein, refers to a system designed to substantially correct for chromatic aberrations.

Figure 1:
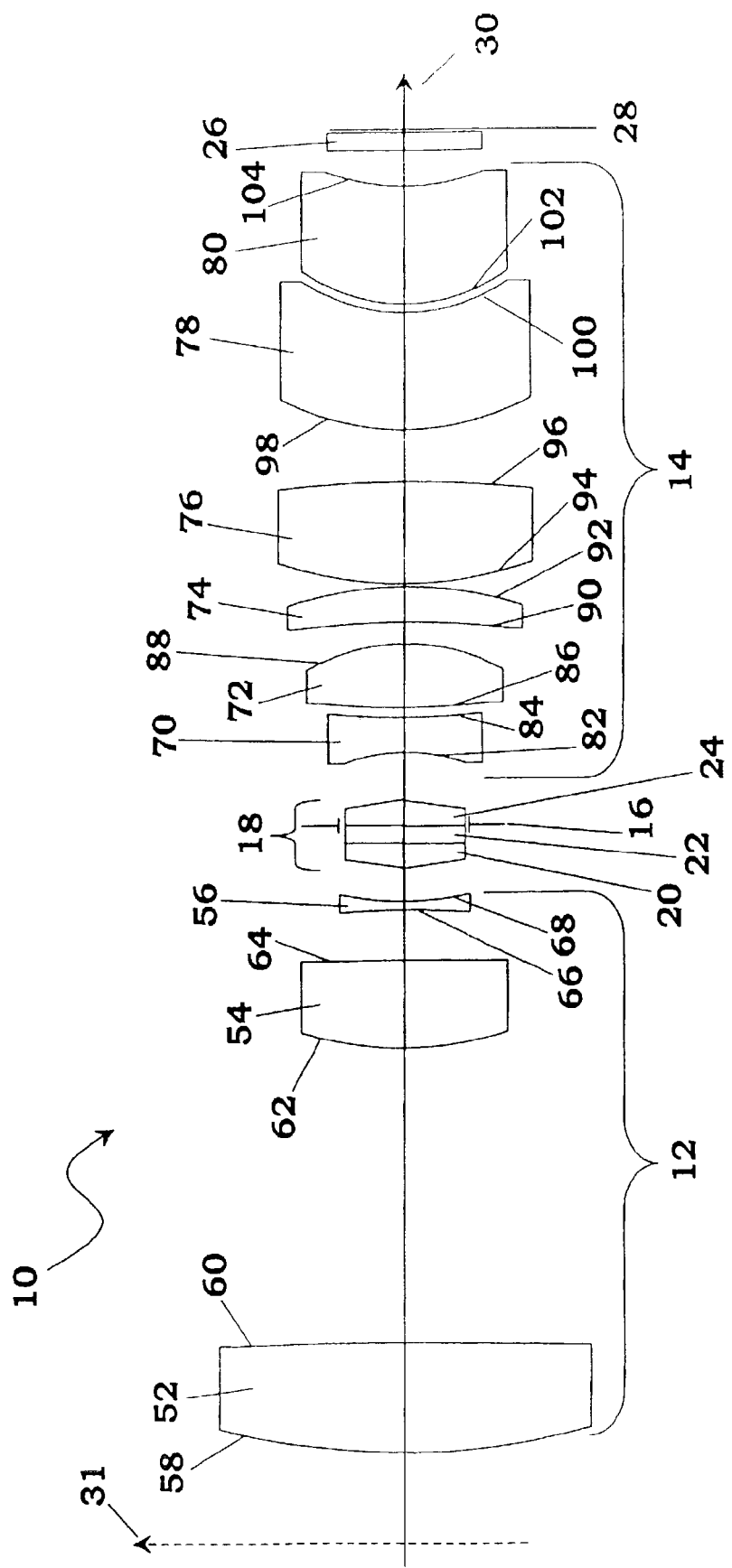
FIG. 1 is a schematic illustration of a first preferred embodiment of the present invention.

The basic concept of the present invention involves forming a plurality of separate images on a single imaging plane simultaneously. FIG. 1 shows a schematic diagram of a first preferred embodiment of the present invention 10.

FIG. 1 shows a schematic diagram cut-away view of a color-corrected imaging lens, consisting of a first lens group 12, a second lens group 14, and an aperture stop 16. Also shown is a filter and prism group 18 inserted at a location substantially coincident with the aperture stop 16. The filter and prism group 18 (also referred to as a beam separating sub-system) is comprised of a first prism 20, a filter set 22, and a second prism 24. Also shown is a second filter set 26 (also referred to as a filtering sub-system), located at a plane that is very close in proximity to the image plane 28 of the optical system 10. Note that all of these optical elements are aligned along an optical axis 30. Note also that the positive direction of the optical axis 30 points to the right on the page, as shown in FIG. 1. Note also that the "up" direction is defined as pointing up on the page, as denoted by the y-axis 31 shown in FIG. 1.

The introduction of the filter and prism group 18 into the optical system 10, at a location substantially coincident with the aperture stop 16 of the system 10, as shown in FIG. 1 causes the optical system 10 to form multiple images simultaneously on the image plane 28. The purpose of the second filter set 26 is to exclude light from one of these multiple images from becoming incident on the portion of the imaging plane corresponding to any of the other images. In this way, the filters comprising the second filter set 26 are said to be matched, as defined herein below, to the filters in the first filter set 22.

Embodiments of the system of this invention are described herein below. Although the embodiments are described for specific wavelength ranges, resulting in the selection of specific component parameters, it should be noted that system of this invention is not limited to those parameter ranges. In the embodiments described herein below, although the characteristics of elements of the embodiment are stated with specificity, it should be noted that the specific value of any of the characteristics of any element of the embodiment is provided to within engineering tolerances. Engineering tolerances as utilized herein include the tolerances within which elements can be procured and the tolerances within which the design performs the desired function.

FIG. 2a depicts a drawing of the first preferred embodiment of the first prism 20, and clearly shows the vertices 32 of the first prism 20, which vertices 32 separate the multiple sections 34 (four in this case) of the first prism 20. FIG. 2b shows a side view of the first prism 20 and clearly shows the flat side 36 of the prism 20 and the optic axis 30. In this first preferred embodiment of the invention 10, the angle between any one of the vertices 32 and the flat side 36 of the first prism 20 is preferably 8.1 degrees. The center thickness of the first prism 20, measured along the optic axis 30, is 5.0 mm. The first prism 20 is centered on the optic axis 30. The first prism 20 is preferably made of glass with an optical index of 1.439 and an Abbe dispersion V-number of 95, such as O'Hara glass S-FPL53. The first prism 20 is preferably square in shape, when viewed along a direction parallel to the optic axis 30, and preferably measures 20 mm across each side. FIG. 2c shows a front view of the first prism 20 and clearly shows the vertices 32 of the first prism 20, which vertices 32 separate the multiple flat sections 34 (four in this case) of the first prism 20. The drawing of the first prism 20 in FIG. 2c is made from the point of view where the positive direction of the optic axis 30 is pointing into the page, away from the reader. Note that the "up" direction is defined as pointing up on the page, as denoted by the y-axis 31 shown in FIG. 2c. Note that the first prism 20 may comprise four separate pieces of glass, each piece of glass comprising one of the sections 34, wherein the four pieces of glass are held together, mechanically or with an adhesive, so that they comprise a first prism 20. It should be noted that the first prism 20 may be also comprised of a single optical element, where the element has multiple flat sections 34 (facets) located opposite from a single substantially flat facet 36.

Figure 3:
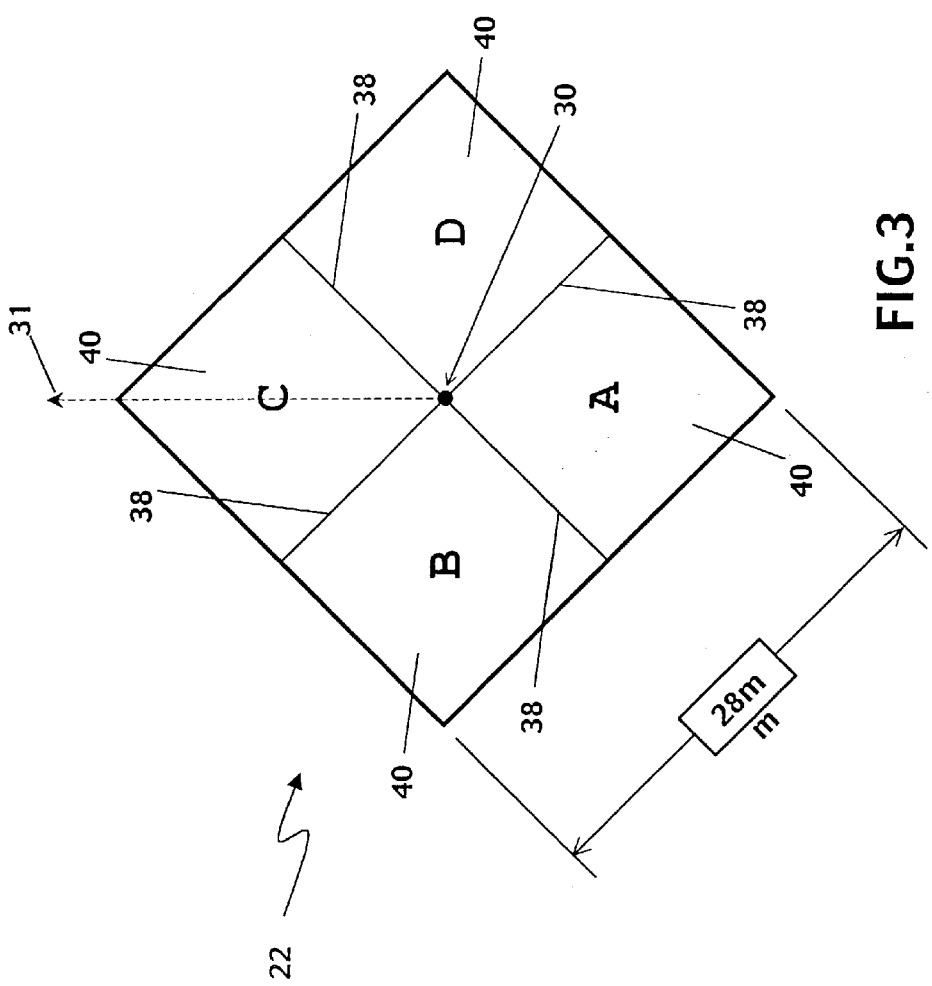
FIG. 3 is a schematic illustration of a first preferred embodiment of the first filter set.

FIG. 3 shows a drawing of a front view of the first preferred embodiment of the first filter plane 22 and clearly shows the vertices 38 of the first filter plane 22, which vertices 38 separate the multiple separate filters 40 (four in this case) of the first filter plane 22 (also referred to as a filter system). The drawing of the filter plane 22 in FIG. 3 is made from the point of view where the positive direction of the optic axis 30 is pointing into the page, away from the reader. Note that the "up" direction is defined as pointing up on the page, as denoted by the y-axis 31 shown in FIG. 3. The first filter plane 22 is preferably square in shape, when viewed along a direction parallel to the optic axis 30, and preferably measures 28 mm across each side. Note that the four filters 40 that comprise the first filter plane 22 are marked A, B, C, and D in FIG. 3. The first filter plane 22 is centered on the optic axis 30. Note that the vertices 38 of the first filter plane 22 and the vertices 32 of the first prism 20 are aligned to be substantially overlapping one another when viewed in a direction along the optic axis 30. The filters comprising the first filter plane 22 are preferably 3.00 mm thick and are preferably made of glass with an optical index of 1.517 and an Abbe dispersion V-number of 64.2, such as Schott glass BK7. Each of the filters 40 may transmit only a certain specific band or bands of wavelengths. Each of the filters 40 may transmit only a certain polarization state or states of light. Each of the filters 40 may transmit only a certain fraction of light. Each of the filters 40 may transmit some combination of wavelengths and/or polarization states.

Figure 4A:
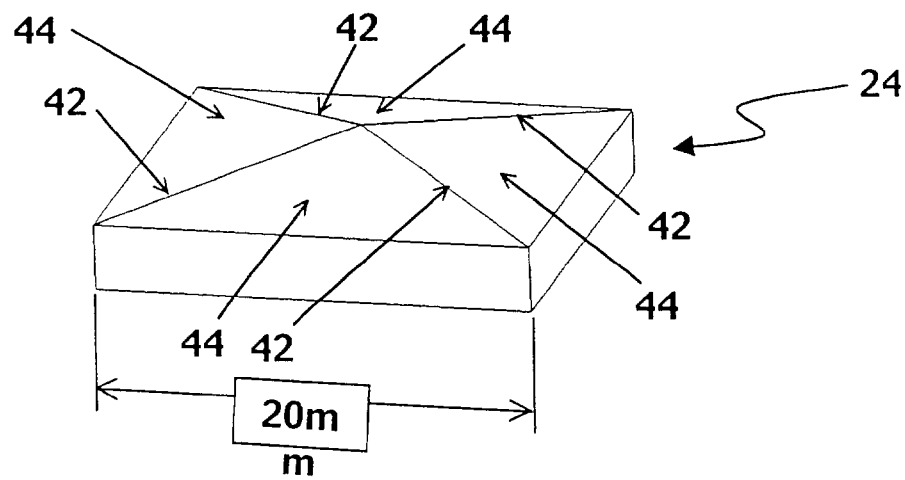
FIG. 4a is a schematic illustration of a first preferred embodiment of the second prism.
Figure 4B:
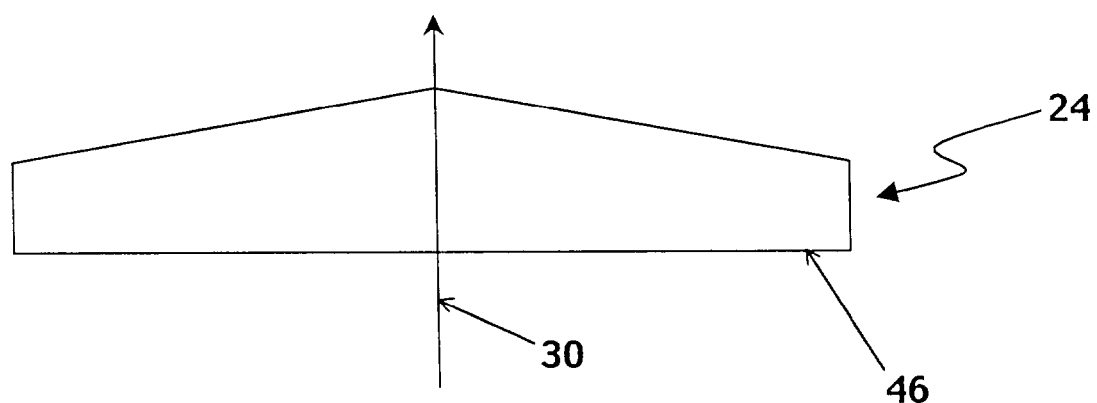
FIG. 4b is a schematic side-view illustration of a first preferred embodiment of the second prism.
Figure 4C:
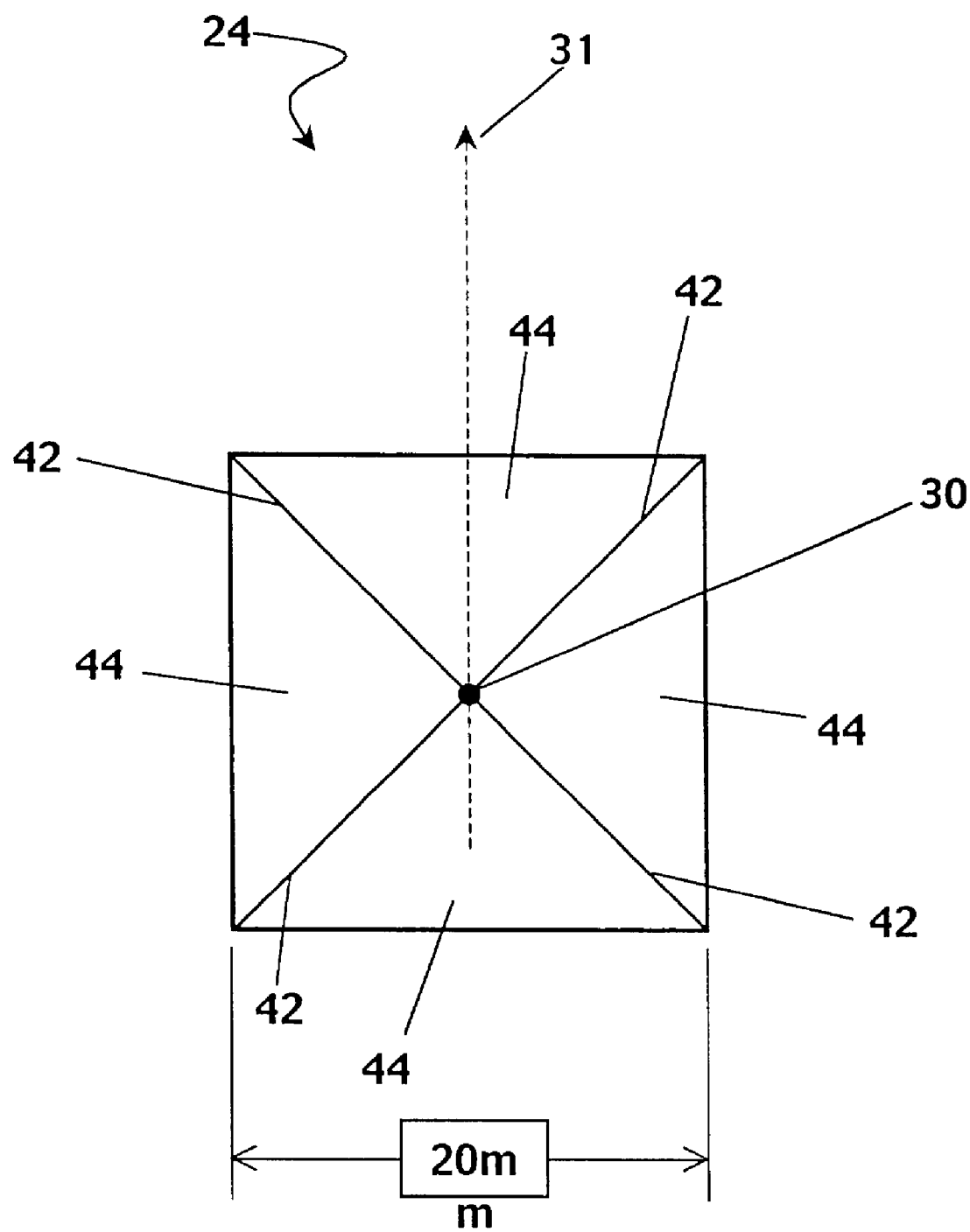
FIG. 4c is a schematic front-view illustration of a first preferred embodiment of the second prism.

FIG. 4a shows a drawing of the first preferred embodiment of the second prism 24, and clearly shows the vertices 42 of the second prism 24, which vertices 42 separate the multiple sections 44 (four in this case) of the second prism 24. FIG. 4b shows a side view of the second prism 24 and clearly shows the flat side 46 of the prism 24 and the optic axis 30. In this first preferred embodiment of the invention 10, the angle between any one of the vertices 42 and the flat side 46 of the second prism 24 is 8.1 degrees. The center thickness of the second prism 24, measured along the optic axis 30, is preferably 5.0 mm. The second prism 24 is centered on the optic axis 30. Note that the vertices 42 of the second prism 24 and the vertices 38 of the first filter plane 22 are aligned to be substantially overlapping one another when viewed in a direction along the optic axis 30. The second prism 24 is preferably made of glass with an optical index of 1.439 and an Abbe dispersion V-number of 95, such as O'Hara glass S-FPL53. The second prism 24 is preferably square in shape, when viewed along a direction parallel to the optic axis 30, and preferably measures 20 mm across each side. FIG. 4c shows a front view of the second prism 24 and clearly shows the vertices 42 of the second prism 24, which vertices 42 separate the multiple flat sections 44 (four in this case) of the second prism 24. The drawing of the second prism 24 in FIG. 4c is made from the point of view where the positive direction of the optic axis 30 is pointing into the page, away from the reader. Note that the "up" direction is defined as pointing up on the page, as denoted by the y-axis 31 shown in FIG. 4c. Note that the second prism 24 may comprise four separate pieces of glass, each piece of glass comprising one of the sections 44, wherein the four pieces of glass are held together, mechanically or with an adhesive, so that they comprise a second prism 24. It should be noted that the second prism 24 may be also comprised of a single optical element, where the element has multiple flat sections 44 (facets) located opposite from a single substantially flat facet 46.

Figure 5:
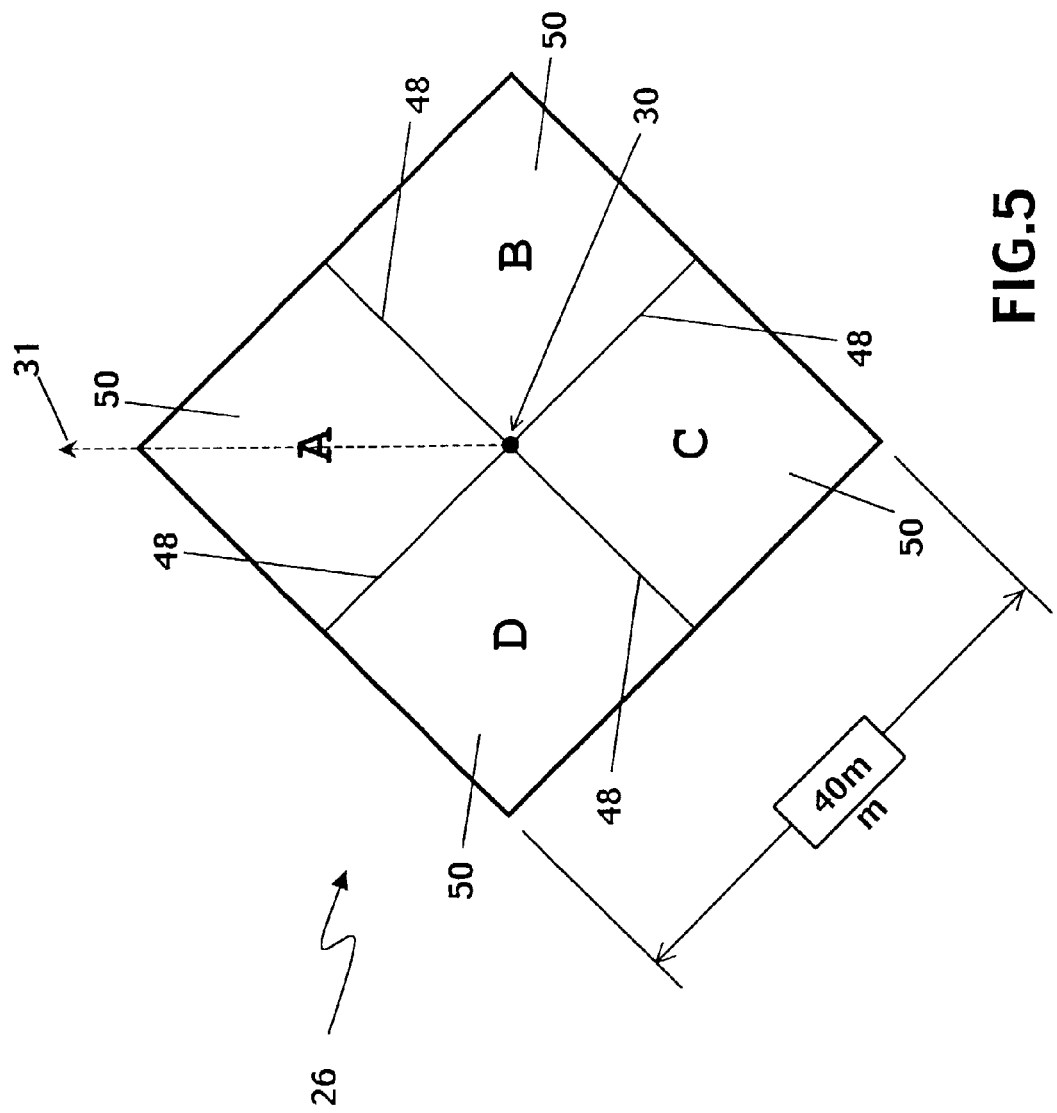
FIG. 5 is a schematic illustration of a first preferred embodiment of the second filter set.

FIG. 5 shows a drawing of the first preferred embodiment of the second filter plane 26 (also referred to as a second filter system), and clearly shows the vertices 48 of the second filter plane 26, which vertices 48 separate the multiple separate filters 50 (four in this case) of the second filter plane 26. The second filter plane 26 is preferably square in shape, when viewed along a direction parallel to the optic axis 30, and preferably measures 40 mm across each side. Note that the four filters 50 are marked A', B', C', and D' in FIG. 5. The second filter plane 26 is centered on the optic axis 30. Note that the vertices 48 of the second filter plane 26 and the vertices 32 of the second prism 24 are aligned to be substantially overlapping one another when viewed in a direction along the optic axis 30. The filters comprising the second filter plane 26 are preferably 3.0 mm thick and are preferably made of glass with an optical index of 1.517 and an Abbe dispersion V-number of 64.2, such as Schott glass BK7. Each of the filters 50 may transmit only a certain specific band or bands of wavelengths. Each of the filters 50 may transmit only a certain polarization state or states of light. Each of the filters 50 may transmit only a certain fraction of light. Each of the filters 50 may transmit some combination of wavelengths and/or polarization states. Note that the actions of the filters 50 are chosen such that filter A' in the second filter plane 26 will transmit light that has been transmitted through filter A in the first filter plane 22, but will not transmit light that has been transmitted through filters B, C, or D in the first filter plane 22. Likewise, filter B' in the second filter plane 26 will transmit light that has been transmitted through filter B in the first filter plane 22, but will not transmit light that has been transmitted through filters A, C, or D in the first filter plane 22. Likewise, filter C' in the second filter plane 26 will transmit light that has been transmitted through filter C in the first filter plane 22, but will not transmit light that has been transmitted through filters A, B, or D in the first filter plane 22. Likewise, filter D' in the second filter plane 26 will transmit light that has been transmitted through filter D in the first filter plane 22, but will not transmit light that has been transmitted through filters A, B, or C in the first filter plane 22.

Referring again to FIG. 1, the first lens group 12 is preferably comprised of a first lens element 52, a second lens element 54, and a third lens element 56.

The first lens element 52 is preferably made of glass with an optical index of 1.529 and an Abbe dispersion V-number of 77.0, such as Schott glass PK51A. The shape of the first surface 58 of the first lens element 52 is preferably convex spherical, with a radius of curvature of 120.00 mm. The shape of the second surface 60 of the first lens element 52 is preferably convex spherical, with a radius of curvature of 950.00 mm. The center thickness of the first lens element 52 is preferably 18.80 mm. The first lens element 52 preferably measures 66 mm in diameter. The center distance, measured along the optic axis 30, between the first lens element 52 and the second lens element 54 is preferably 50.00 mm.

The second lens element 54 is preferably made of glass with an optical index of 1.439 and an Abbe dispersion V-number of 95.0, such as O'Hara glass S-FPL53. The shape of the first surface 62 of the second lens element 54 is preferably convex spherical, with a radius of curvature of 58.00 mm. The shape of the second surface 64 of the second lens element 54 is preferably convex spherical, with a radius of curvature of 971.00 mm. The center thickness of the second lens element 54 is preferably 15.00 mm. The second lens element 54 preferably measures 38 mm in diameter. The center distance, measured along the optic axis 30, between the second lens element 54 and the third lens element 56 is preferably 8.57 mm.

The third lens element 56 is preferably made of glass with an optical index of 1.613 and an Abbe dispersion V-number of 44.3, such as Schott glass KZFSN4. The shape of the first surface 66 of the third lens element 56 is preferably concave spherical, with a radius of curvature of 140.00 mm. The shape of the second surface 68 of the third lens element 56 is preferably concave spherical, with a radius of curvature of 50.00 mm. The center thickness of the third lens element 56 is preferably 1.500 mm. The third lens element 56 preferably measures 26 mm in diameter. The center distance, measured along the optic axis 30, between the third lens element 56 and the first prism 20 is preferably 5.00 mm.

The first prism 20 is preferably oriented, as shown in FIG. 1, with its convex side closest to the third lens element 56. The flat surface 36 of the first prism 20 is preferably in contact with the first filter plane 22. The first filter plane 22 is preferably in contact with the flat surface 46 of the second prism 24. The aperture stop 16 is preferably located at the plane between the first filter plane 22 and the flat surface 46 of the second prism. The aperture stop 16 is preferably a circular aperture with a diameter of 17.0 mm.

The second lens group 14 is preferably comprised of a fourth lens element 70, a fifth lens element 72, a sixth lens element 74, a seventh lens element 76, an eighth lens element 78, and a ninth lens element 80.

The second prism 24 is preferably oriented, as shown in FIG. 1, with its convex side closest to the fourth lens element 70. The center distance, measured along the optic axis 30, between the second prism 24 and the fourth lens element 70 is preferably 7.30 mm.

The fourth lens element 70 is preferably made of glass with an optical index of 1.613 and an Abbe dispersion V-number of 44.3, such as Schott glass KZFSN4. The shape of the first surface 82 of the fourth lens element 70 is preferably concave spherical, with a radius of curvature of 29.00 mm. The shape of the second surface 84 of the fourth lens element 70 is preferably concave spherical, with a radius of curvature of 122.00 mm. The center thickness of the fourth lens element 70 is preferably 6.00 mm. The fourth lens element 70 preferably measures 30 mm in diameter. The center distance, measured along the optic axis 30, between the fourth lens element 70 and the fifth lens element 72 is preferably 1.70 mm.

The fifth lens element 72 is preferably made of glass with an optical index of 1.439 and an Abbe dispersion V-number of 95.0, such as O'Hara glass S-FPL53. The shape of the first surface 86 of the fifth lens element 72 is preferably convex spherical, with a radius of curvature of 130.00 mm. The shape of the second surface 88 of the fifth lens element 72 is preferably convex spherical, with a radius of curvature of 33.00 mm. The center thickness of the fifth lens element 72 is preferably 11.00 mm. The fifth lens element 72 preferably measures 38 mm in diameter. The center distance, measured along the optic axis 30, between the fifth lens element 72 and the sixth lens element 74 is preferably 3.70 mm.

The sixth lens element 74 is preferably made of glass with an optical index of 1.613 and an Abbe dispersion V-number of 44.3, such as Schott glass KZFSN4. The shape of the first surface 90 of the sixth lens element 74 is preferably concave spherical, with a radius of curvature of 139.00 mm. The shape of the second surface 92 of the sixth lens element 74 is preferably convex spherical, with a radius of curvature of 64.30 mm. The center thickness of the sixth lens element 74 is preferably 6.00 mm. The sixth lens element 74 preferably measures 44 mm in diameter. The center distance, measured along the optic axis 30, between the sixth lens element 74 and the seventh lens element 76 is preferably 0.50 mm.

The seventh lens element 76 is preferably made of glass with an optical index of 1.439 and an Abbe dispersion V-number of 95.0, such as O'Hara glass S-FPL53. The shape of the first surface 94 of the seventh lens element 76 is preferably convex spherical, with a radius of curvature of 65.00 mm. The shape of the second surface 96 of the seventh lens element 76 is preferably convex spherical, with a radius of curvature of 187.00 mm. The center thickness of the seventh lens element 76 is preferably 17.2 mm. The seventh lens element 76 preferably measures 46 mm in diameter. The center distance, measured along the optic axis 30, between the seventh lens element 76 and the eighth lens element 78 is preferably 8.87 mm.

The eighth lens element 78 is preferably made of glass with an optical index of 1.439 and an Abbe dispersion V-number of 95.0, such as O'Hara glass S-FPL53. The shape of the first surface 98 of the eighth lens element 78 is preferably convex spherical, with a radius of curvature of 44.00 mm. The shape of the second surface 100 of the eighth lens element 78 is preferably concave spherical, with a radius of curvature of 31.00 mm. The center thickness of the eighth lens element 78 is preferably 20.000 mm. The eighth lens element 78 preferably measures 46 mm in diameter. The center distance, measured along the optic axis 30, between the eighth lens element 78 and the ninth lens element 80 is preferably 1.50 mm.

The ninth lens element 80 is preferably made of glass with an optical index of 1.529 and an Abbe dispersion V-number of 77.0, such as Schott glass PK51A. The shape of the first surface 102 of the ninth lens element 80 is preferably convex spherical, with a radius of curvature of 30.00 mm. The shape of the second surface 104 of the ninth lens element 80 is preferably concave spherical, with a radius of curvature of 38.00 mm. The ninth lens element 80 preferably measures 40 mm in diameter. The center thickness of the ninth lens element 80 is preferably 20.00 mm. The center distance, measured along the optic axis 30, between the ninth lens element 80 and the second filter plane 26 is preferably 6.17 mm.

The center distance, measured along the optic axis 30, between the second filter plane 26 and the imaging plane 28 is preferably 0.526 mm.

Figure 6:
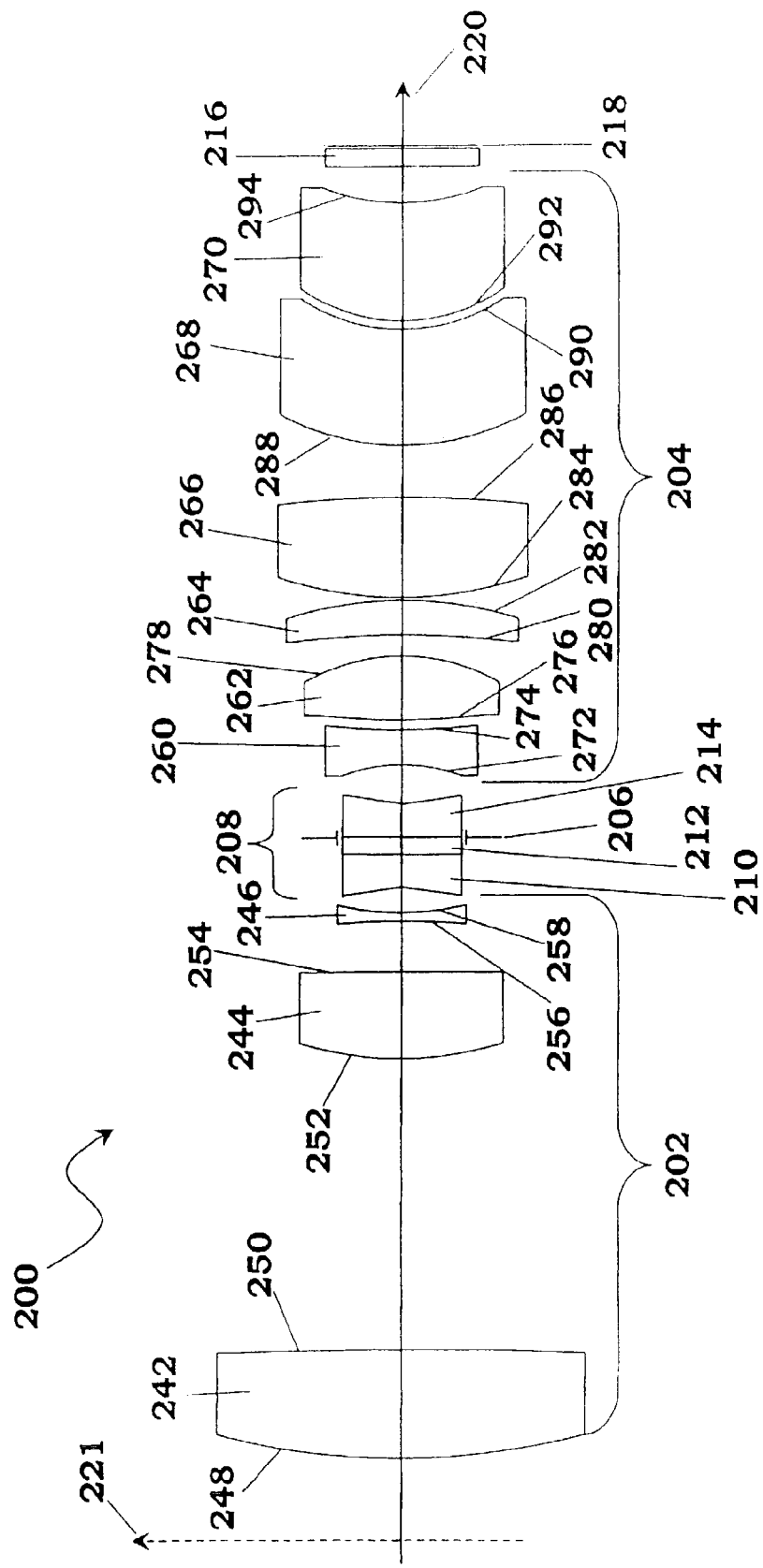
FIG. 6 is a schematic illustration of a second preferred embodiment of the present invention.

FIG. 6 shows a schematic diagram of a second preferred embodiment of the present invention 200. Note that the only difference between the first preferred embodiment of the present invention 10 and the second preferred embodiment of the present invention 200 is that the filter and prism group 18 of the first embodiment of the present invention 10 has been changed in the second embodiment of the present invention 200. All other elements of the two embodiments are identical.

FIG. 6 shows a schematic diagram cut-away view of a color-corrected imaging lens, consisting of a first lens group 202, a second lens group 204, and an aperture stop 206. Also shown is a filter and prism group 208 inserted at a location substantially coincident with the aperture stop 206. The filter and prism group 208 is comprised of a first prism 210, a filter set 212, and a second prism 214. Also shown is a second filter set 216, located at a plane that is very close in proximity to the image plane 218 of the optical system 200. Note that all of these optical elements are aligned along an optical axis 220. Note also that the positive direction of the optical axis 220 points to the right on the page, as shown in FIG. 6. Note also that the "up" direction is defined as pointing up on the page, as denoted by the y-axis 221 shown in FIG. 6.

The introduction of the filter and prism group 208 into the optical system 200, at a location substantially coincident with the aperture stop 206 of the system 200, as shown in FIG. 6, causes the optical system 200 to form multiple images simultaneously on the image plane 218. The purpose of the second filter set 216 is to exclude light from one of these multiple images from becoming incident on the portion of the imaging plane corresponding to any of the other images. In this way, the filters comprising the second filter set 216 are said to be matched to the filters in the first filter set 212.

Figure 7A:
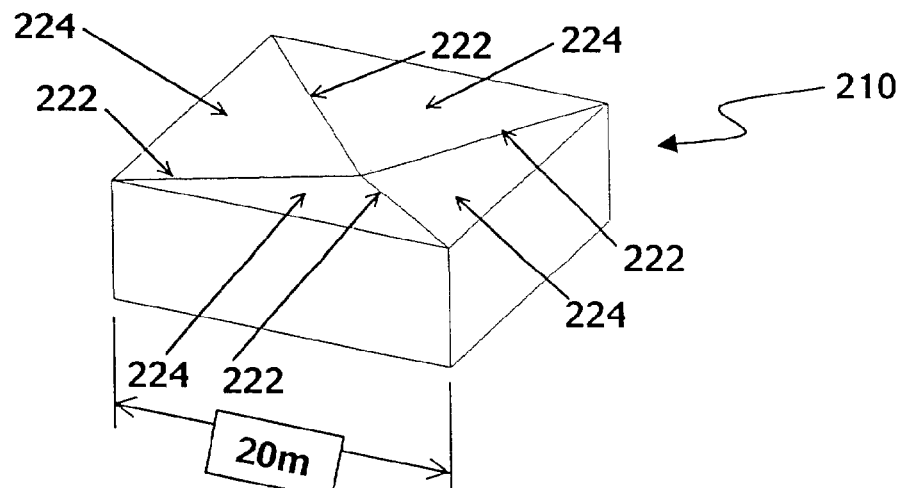
FIG. 7a is a schematic illustration of a second preferred embodiment of the first prism.
Figure 7B:
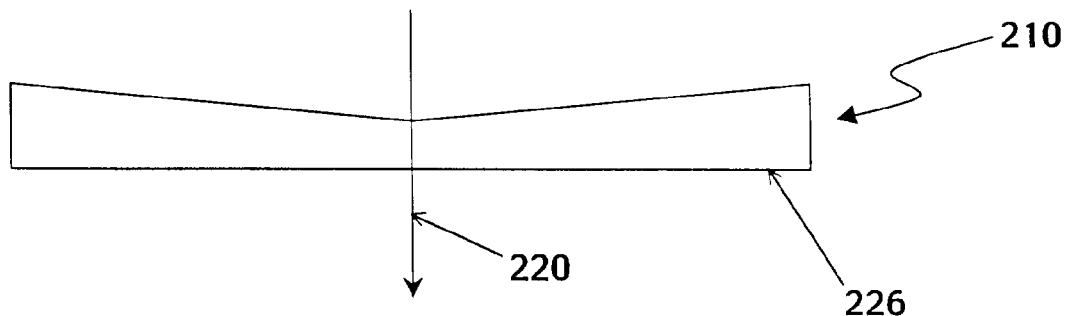
FIG. 7b is a schematic side-view illustration of a second preferred embodiment of the first prism.
Figure 7C:
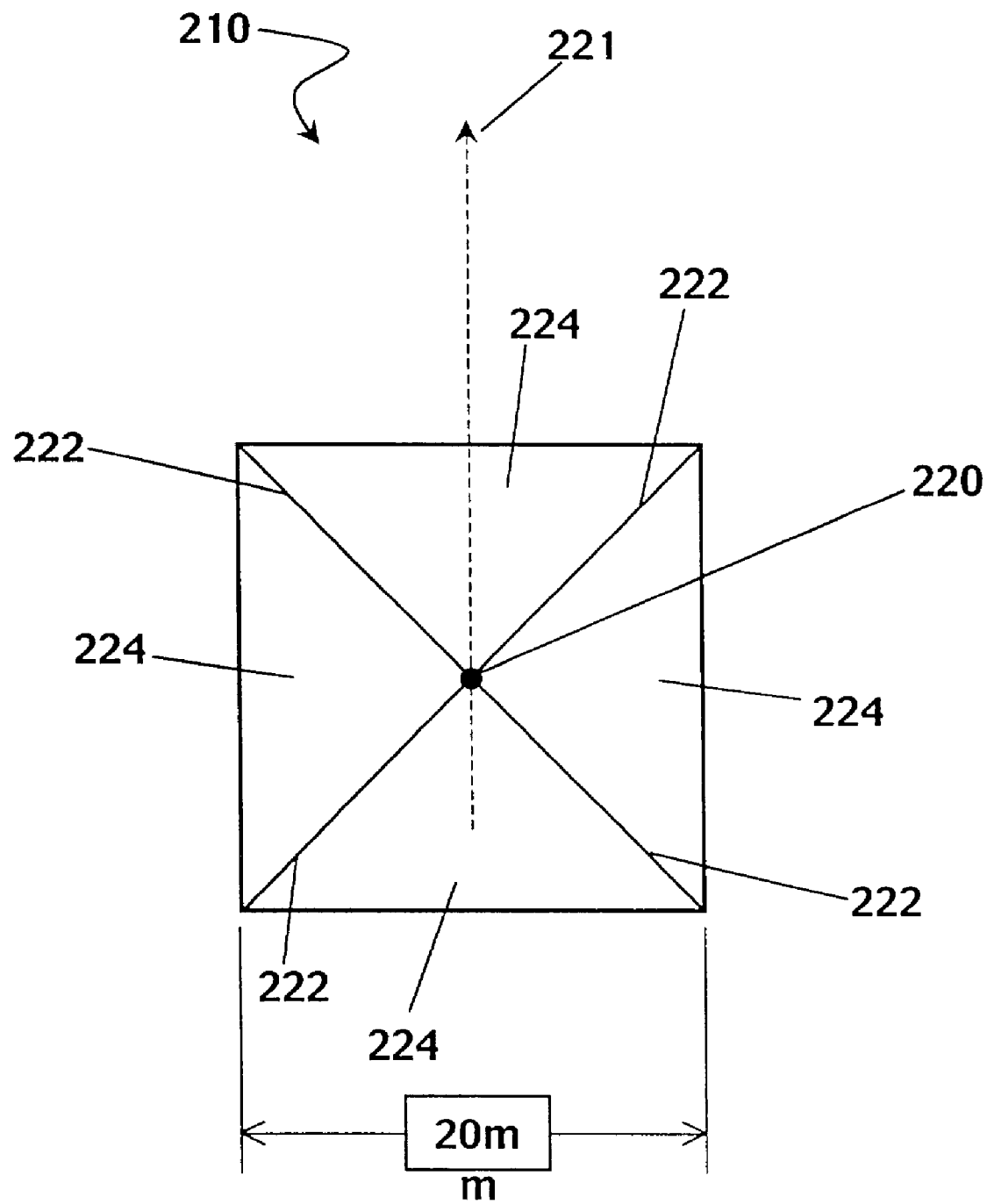
FIG. 7c is a schematic front-view illustration of a second preferred embodiment of the first prism.

FIG. 7a shows a drawing of the second preferred embodiment of the first prism 210, and clearly shows the vertices 222 of the first prism 210, which vertices 222 separate the multiple sections 224 (four in this case) of the first prism 210. FIG. 7b shows a side view of the first prism 210 and clearly shows the flat side 226 of the prism 210 and the optic axis 220. In the second preferred embodiment of the invention 200, the angle between any one of the vertices 222 and the flat side 226 of the first prism 210 is 8.1 degrees. The center thickness of the first prism 210, measured along the optic axis 220, is 5.0 mm. The first prism 210 is centered on the optic axis 220. The first prism 210 is preferably made of glass with an optical index of 1.439 and an Abbe dispersion V-number of 95, such as O'Hara glass S-FPL53. The first prism 210 is preferably square in shape, when viewed along a direction parallel to the optic axis 220, and preferably measures 20 mm across each side. FIG. 7c shows a front view of the first prism 210 and clearly shows the vertices 222 of the first prism 210, which vertices 222 separate the multiple sections 224 (four in this case) of the first prism 210. The drawing of the first prism 210 in FIG. 7c is made from the point of view where the positive direction of the optic axis 220 is pointing into the page, away from the reader. Note that the "up" direction is defined as pointing up on the page, as denoted by the y-axis 221 shown in FIG. 7c. Note that the first prism 210 may comprise four separate pieces of glass, each piece of glass comprising one of the sections 224, wherein the four pieces of glass are held together, mechanically or with an adhesive, so that they comprise a first prism 210.

Figure 8:
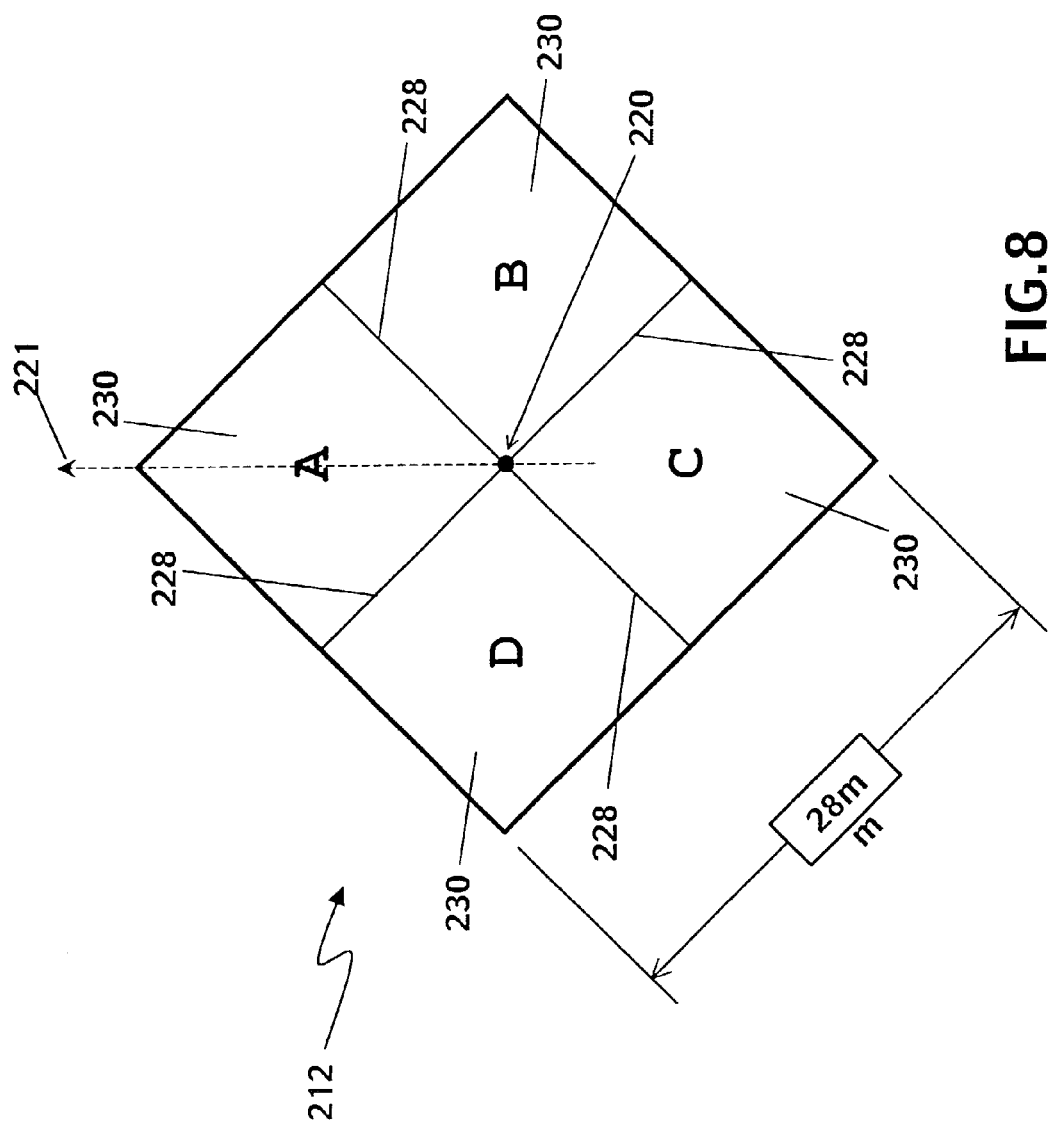
FIG. 8 is a schematic illustration of a second preferred embodiment of the first filter set.

FIG. 8 shows a drawing of the second preferred embodiment of the first filter plane 212, and clearly shows the vertices 228 of the first filter plane 212, which vertices 228 separate the multiple separate filters 230 (four in this case) of the first filter plane 212. The drawing of the filter plane 212 in FIG. 8 is made from the point of view where the positive direction of the optic axis 220 is pointing into the page, away from the reader. Note that the "up" direction is defined as pointing up on the page, as denoted by the y-axis 221 shown in FIG. 8. The first filter plane 212 is preferably square in shape, when viewed along a direction parallel to the optic axis 220, and preferably measures 28 mm across each side. Note that the four filters 230 that comprise the first filter plane 212 are marked A, B, C, and D in FIG. 3. The first filter plane 212 is centered on the optic axis 220. Note that the vertices 228 of the first filter plane 212 and the vertices 222 of the first prism 210 are aligned to be substantially overlapping one another when viewed in a direction along the optic axis 220. The filters comprising the first filter plane 212 are preferably 3.00 mm thick and are preferably made of glass with an optical index of 1.517 and an Abbe dispersion V-number of 64.2, such as Schott glass BK7. Each of the filters 230 may transmit only a certain specific band or bands of wavelengths. Each of the filters 230 may transmit only a certain polarization state or states of light. Each of the filters 230 may transmit only a certain fraction of light. Each of the filters 230 may transmit some combination of wavelengths and/or polarization states.

Figure 9A:
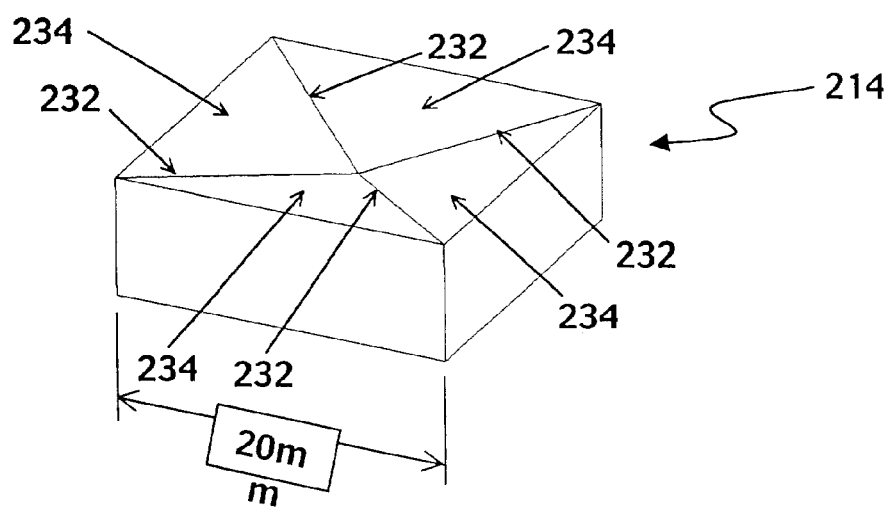
FIG. 9a is a schematic illustration of a second preferred embodiment of the second prism.
Figure 9B:
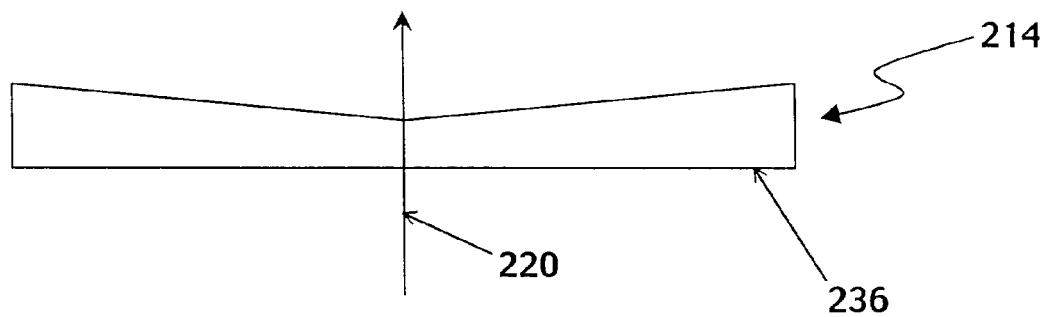
FIG. 9b is a schematic side-view illustration of a second preferred embodiment of the second prism.
Figure 9C:
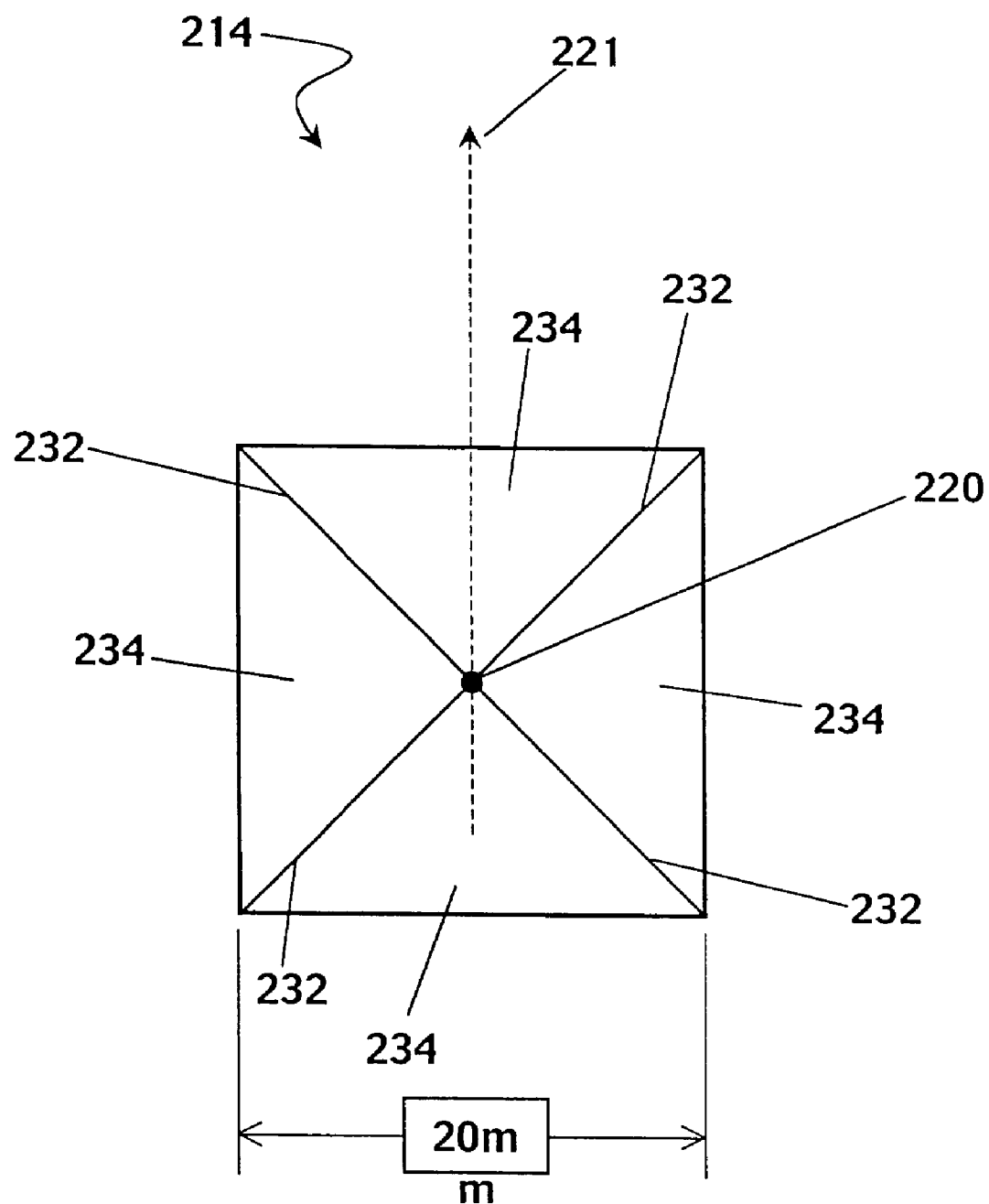
FIG. 9c is a schematic front-view illustration of a second preferred embodiment of the second prism.

FIG. 9a shows a drawing of the second preferred embodiment of the second prism 214, and clearly shows the vertices 232 of the second prism 214, which vertices 232 separate the multiple sections 234 (four in this case) of the second prism 214. FIG. 9b shows a side view of the second prism 214 and clearly shows the flat side 236 of the prism 214 and the optic axis 220. In this second preferred embodiment of the invention 200, the angle between any one of the vertices 232 and the flat side 236 of the second prism 214 is 8.1 degrees. The center thickness of the second prism 214, measured along the optic axis 220, is preferably 5.0 mm. The second prism 214 is centered on the optic axis 220. Note that the vertices 232 of the second prism 214 and the vertices 228 of the first filter plane 212 are aligned to be substantially overlapping one another when viewed in a direction along the optic axis 220. The second prism 214 is preferably made of glass with an optical index of 1.439 and an Abbe dispersion V-number of 95, such as O'Hara glass S-FPL53. The second prism 214 is preferably square in shape, when viewed along a direction parallel to the optic axis 220, and preferably measures 20 mm across each side. FIG. 9c shows a front view of the second prism 214 and clearly shows the vertices 232 of the second prism 214, which vertices 232 separate the multiple sections 234 (four in this case) of the second prism 214. The drawing of the second prism 214 in FIG. 9c is made from the point of view where the positive direction of the optic axis 220 is pointing into the page, away from the reader. Note that the "up" direction is defined as pointing up on the page, as denoted by the y-axis 221 shown in FIG. 9c. Note that the second prism 214 may comprise four separate pieces of glass, each piece of glass comprising one of the sections 234, wherein the four pieces of glass are held together, mechanically or with an adhesive, so that they comprise a second prism 214.

Figure 10:
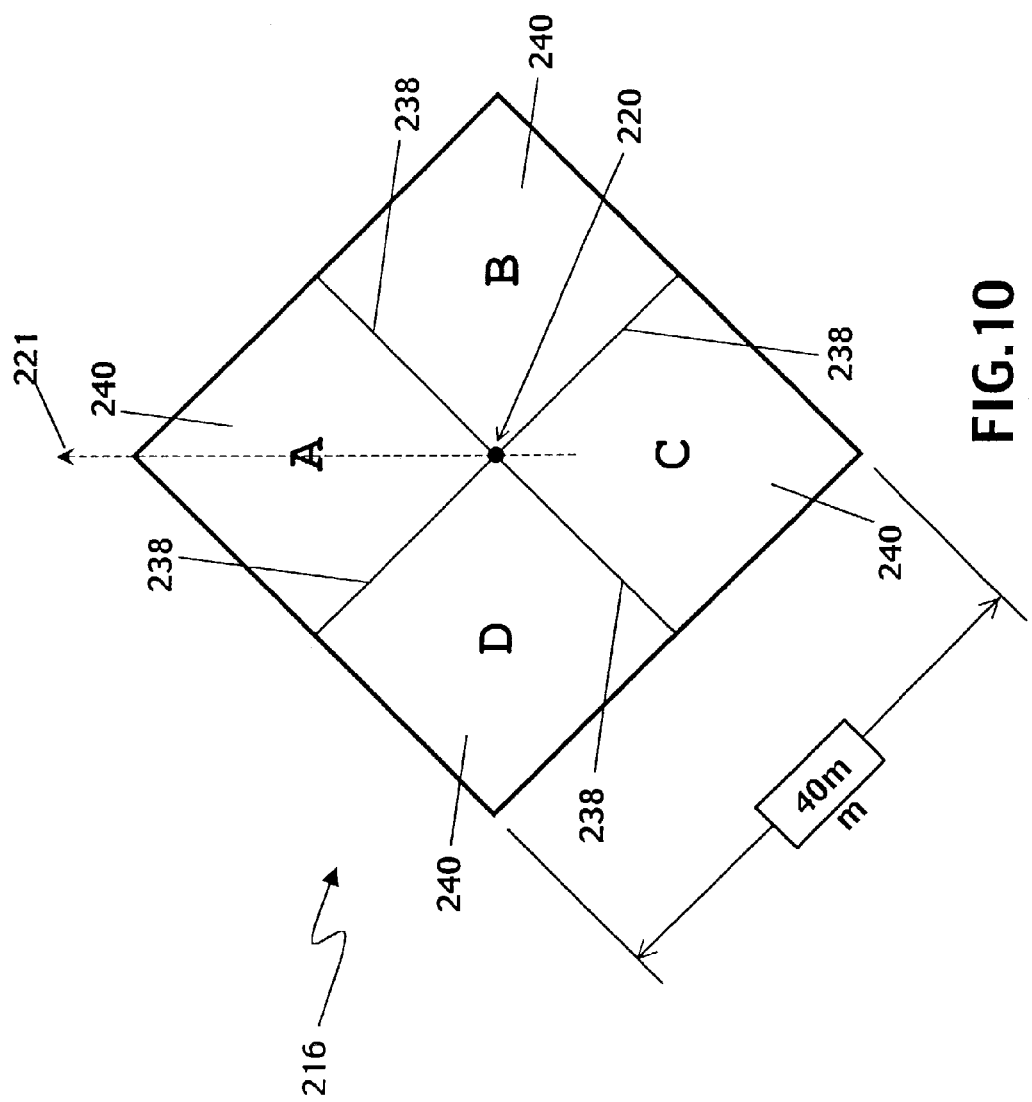
FIG. 10 is a schematic illustration of a second preferred embodiment of the second filter set.

FIG. 10 shows a drawing of the second preferred embodiment of the second filter plane 216, and clearly shows the vertices 238 of the second filter plane 216, which vertices 238 separate the multiple separate filters 240 (four in this case) of the second filter plane 216. The second filter plane 216 is preferably square in shape, when viewed along a direction parallel to the optic axis 220, and preferably measures 40 mm across each side. Note that the four filters 240 are marked A', B', C', and D' in FIG. 10. The second filter plane 216 is centered on the optic axis 220. Note that the vertices 238 of the second filter plane 216 and the vertices 222 of the second prism 214 are aligned to be substantially overlapping one another when viewed in a direction along the optic axis 220. The filters comprising the second filter plane 216 are preferably 3.0 mm thick and are preferably made of glass with an optical index of 1.517 and an Abbe dispersion V-number of 64.2, such as Schott glass BK7. Each of the filters 240 may transmit only a certain specific band or bands of wavelengths. Each of the filters 240 may transmit only a certain polarization state or states of light. Each of the filters 240 may transmit only a certain fraction of light. Each of the filters 240 may transmit some combination of wavelengths and/or polarization states. Note that the actions of the filters 240 are chosen such that filter A' in the second filter plane 216 will transmit light that has been transmitted through filter A in the first filter plane 212, but will not transmit light that has been transmitted through filters B, C, or D in the first filter plane 212. Likewise, filter B' in the second filter plane 216 will transmit light that has been transmitted through filter B in the first filter plane 212, but will not transmit light that has been transmitted through filters A, C, or D in the first filter plane 212. Likewise, filter C' in the second filter plane 216 will transmit light that has been transmitted through filter C in the first filter plane 212, but will not transmit light that has been transmitted through filters A, B, or D in the first filter plane 212. Likewise, filter D' in the second filter plane 216 will transmit light that has been transmitted through filter D in the first filter plane 212, but will not transmit light that has been transmitted through filters A, B, or C in the first filter plane 212.

Referring again to FIG. 6, the first lens group 202 is preferably comprised of a first lens element 242, a second lens element 244, and a third lens element 246.

The first lens element 242 is preferably made of glass with an optical index of 1.529 and an Abbe dispersion V-number of 77.0, such as Schott glass PK51A. The shape of the first surface 248 of the first lens element 242 is preferably convex spherical, with a radius of curvature of 120.00 mm. The shape of the second surface 250 of the first lens element 242 is preferably convex spherical, with a radius of curvature of 950.00 mm. The center thickness of the first lens element 242 is preferably 18.80 mm. The first lens element 242 preferably measures 66 mm in diameter. The center distance, measured along the optic axis 220, between the first lens element 242 and the second lens element 244 is preferably 50.00 mm.

The second lens element 244 is preferably made of glass with an optical index of 1.439 and an Abbe dispersion V-number of 95.0, such as O'Hara glass S-FPL53. The shape of the first surface 252 of the second lens element 244 is preferably convex spherical, with a radius of curvature of 58.00 mm. The shape of the second surface 254 of the second lens element 244 is preferably convex spherical, with a radius of curvature of 971.00 mm. The center thickness of the second lens element 244 is preferably 15.00 mm. The second lens element 244 preferably measures 38 mm in diameter. The center distance, measured along the optic axis 220, between the second lens element 244 and the third lens element 246 is preferably 8.57 mm.

The third lens element 246 is preferably made of glass with an optical index of 1.613 and an Abbe dispersion V-number of 44.3, such as Schott glass KZFSN4. The shape of the first surface 256 of the third lens element 246 is preferably concave spherical, with a radius of curvature of 140.00 mm. The shape of the second surface 258 of the third lens element 246 is preferably concave spherical, with a radius of curvature of 50.00 mm. The center thickness of the third lens element 246 is preferably 1.500 mm. The third lens element 246 preferably measures 26 mm in diameter. The center distance, measured along the optic axis 220, between the third lens element 246 and the first prism 210 is preferably 5.00 mm.

The first prism 210 is preferably oriented, as shown in FIG. 6, with its concave side closest to the third lens element 246. The flat surface 226 of the first prism 210 is preferably in contact with the first filter plane 212. The first filter plane 212 is preferably in contact with the flat surface 236 of the second prism 214. The aperture stop 206 is preferably located at the plane between the first filter plane 212 and the flat surface 236 of the second prism. The aperture stop 206 is preferably a circular aperture with a diameter of 17.0 mm.

The second lens group 204 is preferably comprised of a fourth lens element 260, a fifth lens element 262, a sixth lens element 264, a seventh lens element 266, an eighth lens element 268, and a ninth lens element 270.

The second prism 214 is preferably oriented, as shown in FIG. 6, with its concave side closest to the fourth lens element 260. The center distance, measured along the optic axis 220, between the second prism 214 and the fourth lens element 260 is preferably 7.30 mm.

The fourth lens element 260 is preferably made of glass with an optical index of 1.613 and an Abbe dispersion V-number of 44.3, such as Schott glass KZFSN4. The shape of the first surface 272 of the fourth lens element 260 is preferably concave spherical, with a radius of curvature of 29.00 mm. The shape of the second surface 274 of the fourth lens element 260 is preferably concave spherical, with a radius of curvature of 122.00 mm. The center thickness of the fourth lens element 260 is preferably 6.00 mm. The fourth lens element 260 preferably measures 30 mm in diameter. The center distance, measured along the optic axis 220, between the fourth lens element 260 and the fifth lens element 262 is preferably 1.70 mm.

The fifth lens element 262 is preferably made of glass with an optical index of 1.439 and an Abbe dispersion V-number of 95.0, such as O'Hara glass S-FPL53. The shape of the first surface 276 of the fifth lens element 262 is preferably convex spherical, with a radius of curvature of 130.00 mm. The shape of the second surface 278 of the fifth lens element 262 is preferably convex spherical, with a radius of curvature of 33.00 mm. The center thickness of the fifth lens element 262 is preferably 11.00 mm. The fifth lens element 262 preferably measures 38 mm in diameter. The center distance, measured along the optic axis 220, between the fifth lens element 262 and the sixth lens element 264 is preferably 3.70 mm.

The sixth lens element 264 is preferably made of glass with an optical index of 1.613 and an Abbe dispersion V-number of 44.3, such as Schott glass KZFSN4. The shape of the first surface 280 of the sixth lens element 264 is preferably concave spherical, with a radius of curvature of 139.00 mm. The shape of the second surface 282 of the sixth lens element 264 is preferably convex spherical, with a radius of curvature of 64.30 mm. The center thickness of the sixth lens element 264 is preferably 6.00 mm. The sixth lens element 264 preferably measures 44 mm in diameter. The center distance, measured along the optic axis 220, between the sixth lens element 264 and the seventh lens element 266 is preferably 0.50 mm.

The seventh lens element 266 is preferably made of glass with an optical index of 1.439 and an Abbe dispersion V-number of 95.0, such as O'Hara glass S-FPL53. The shape of the first surface 284 of the seventh lens element 266 is preferably convex spherical, with a radius of curvature of 65.00 mm. The shape of the second surface 286 of the seventh lens element 266 is preferably convex spherical, with a radius of curvature of 187.00 mm. The center thickness of the seventh lens element 266 is preferably 17.2 mm. The seventh lens element 266 preferably measures 46 mm in diameter. The center distance, measured along the optic axis 220, between the seventh lens element 266 and the eighth lens element 268 is preferably 8.87 mm.

The eighth lens element 268 is preferably made of glass with an optical index of 1.439 and an Abbe dispersion V-number of 95.0, such as O'Hara glass S-FPL53. The shape of the first surface 288 of the eighth lens element 268 is preferably convex spherical, with a radius of curvature of 44.00 mm. The shape of the second surface 290 of the eighth lens element 268 is preferably concave spherical, with a radius of curvature of 31.00 mm. The center thickness of the eighth lens element 268 is preferably 20.000 mm. The eighth lens element 268 preferably measures 46 mm in diameter. The center distance, measured along the optic axis 220, between the eighth lens element 268 and the ninth lens element 270 is preferably 1.50 mm.

The ninth lens element 270 is preferably made of glass with an optical index of 1.529 and an Abbe dispersion V-number of 77.0, such as Schott glass PK51A. The shape of the first surface 292 of the ninth lens element 270 is preferably convex spherical, with a radius of curvature of 30.00 mm. The shape of the second surface 294 of the ninth lens element 270 is preferably concave spherical, with a radius of curvature of 38.00 mm. The ninth lens element 270 preferably measures 40 mm in diameter. The center thickness of the ninth lens element 270 is preferably 20.00 mm. The center distance, measured along the optic axis 220, between the ninth lens element 270 and the second filter plane 216 is preferably 6.17 mm.

The center distance, measured along the optic axis 220, between the second filter plane 216 and the imaging plane 218 is preferably 0.526 mm.

Following is a description of the concept of the invention, which description should provide the reader with enough information to allow the realization of a wide variety of further other embodiments within the spirit and scope of the invention.

The basic concept of the invention involves inserting a prism and filter group into an imaging lens system at a location substantially coincident with the aperture stop of the imaging lens system and inserting a matched filter plane at a location close in proximity to the imaging plane of the imaging lens system.

Figure 11:
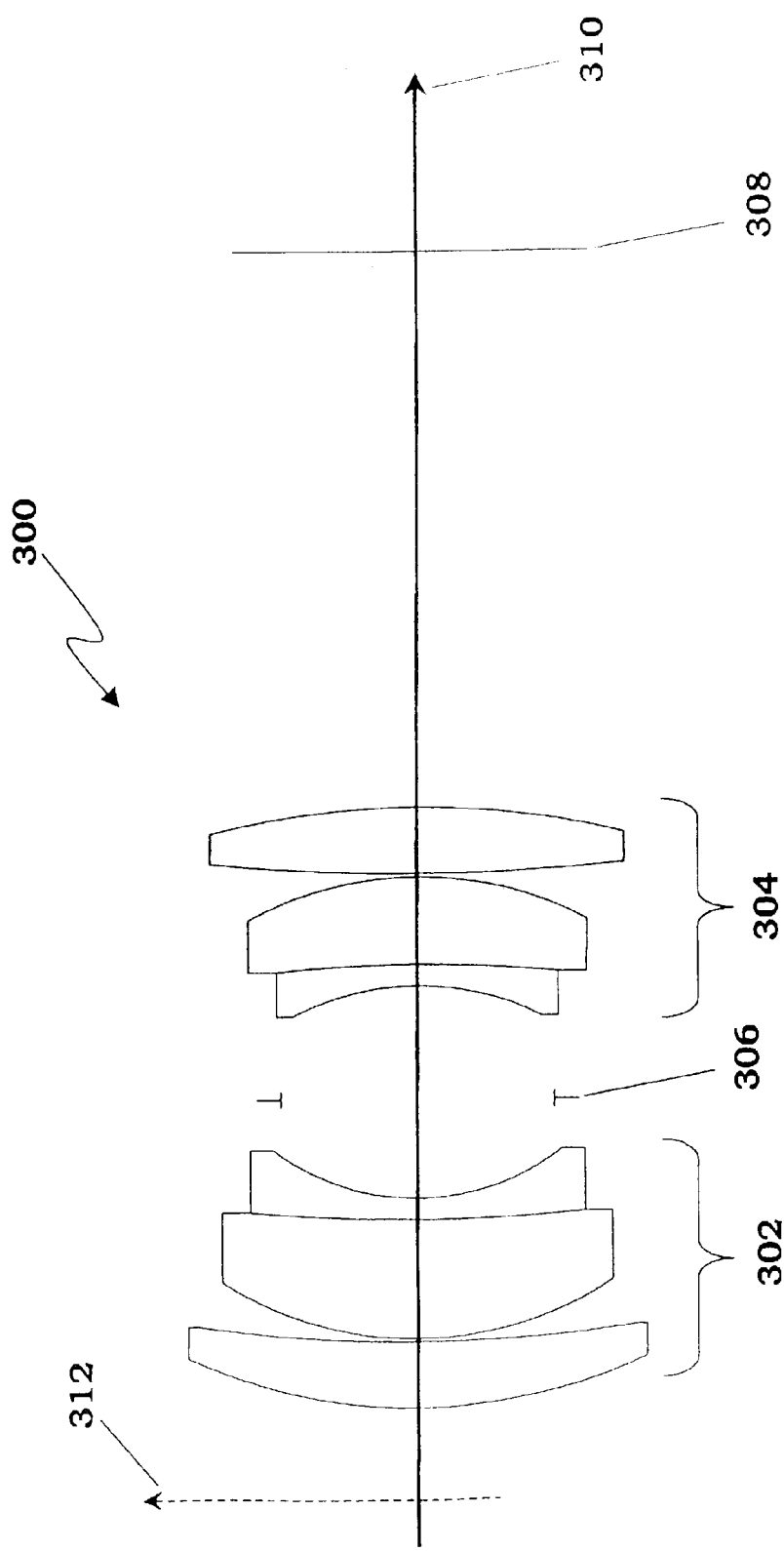
FIG. 11 is a schematic illustration of a side view of a typical imaging lens system.

FIG. 11 shows a side view of a typical imaging lens system 300. This lens system 300 comprises a first lens group 302, a second lens group 304, an aperture stop 306, and an imaging plane 308. All the components of the imaging lens system are centered on an optic axis 310. Note that the positive direction of the optical axis 310 points to the right on the page, as shown in FIG. 11. Note also that the "up" direction is defined as pointing up on the page, as denoted by the y-axis 312 shown in FIG. 11.

Figure 12:
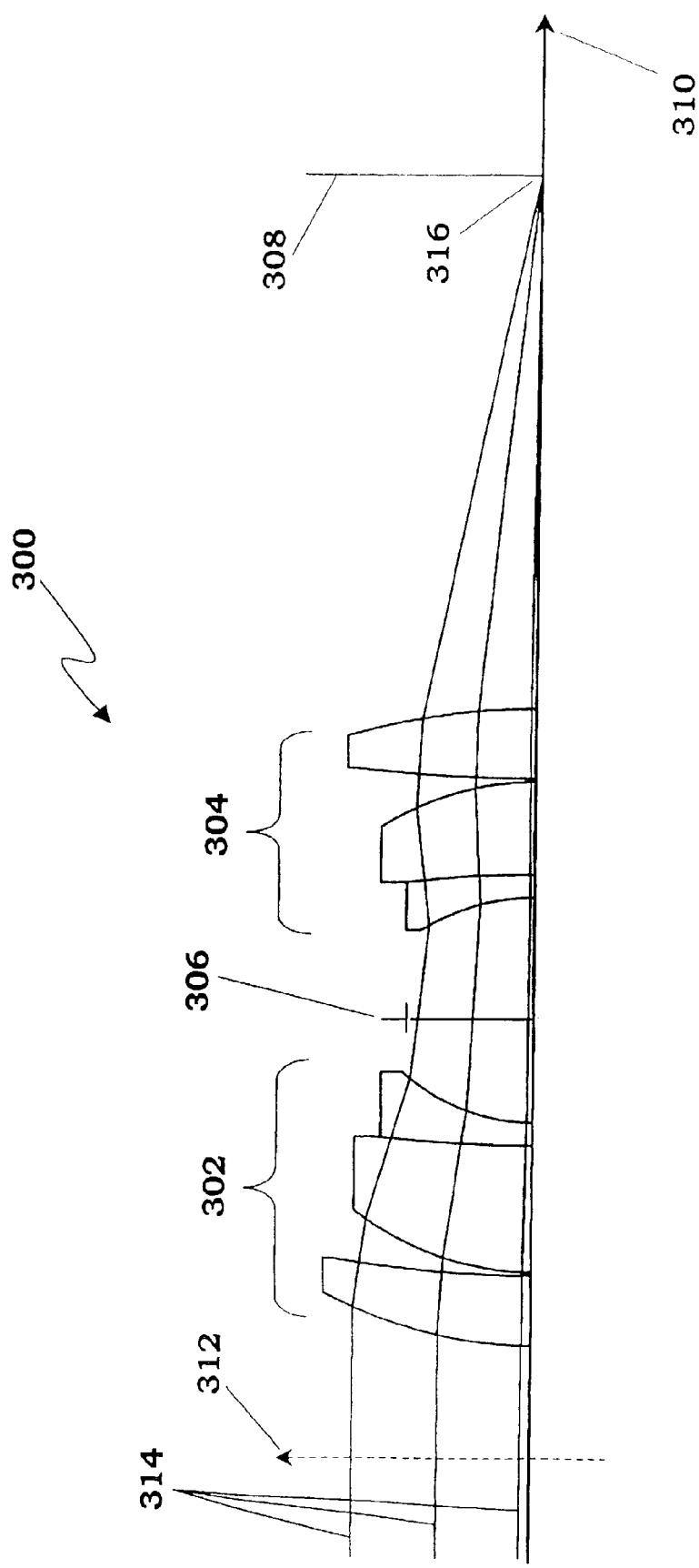
FIG. 12 is a schematic illustration of a cutaway side view of the top portion of a typical imaging lens system.

FIG. 12 shows a cutaway side view of the top portion of the same imaging system. Only the portion of the lens system 300 above the optic axis 310 is shown in FIG. 12. Light rays 314 from a distant, on-axis object are shown entering the lens system 300. As the light rays 314 pass through the first lens group 302, the aperture stop 306, and the second lens group 304, they are imaged and come to a focal point 316 on the image plane 308. As is well understood in the field of imaging optics, the light rays 314 from a distant on-axis object are imaged with a rotationally-symmetric imaging lens system 300 and come to a focus at a point 316 that is substantially coincident with the intersection of the imaging plane 308 and the optic axis 310.

Figure 13:
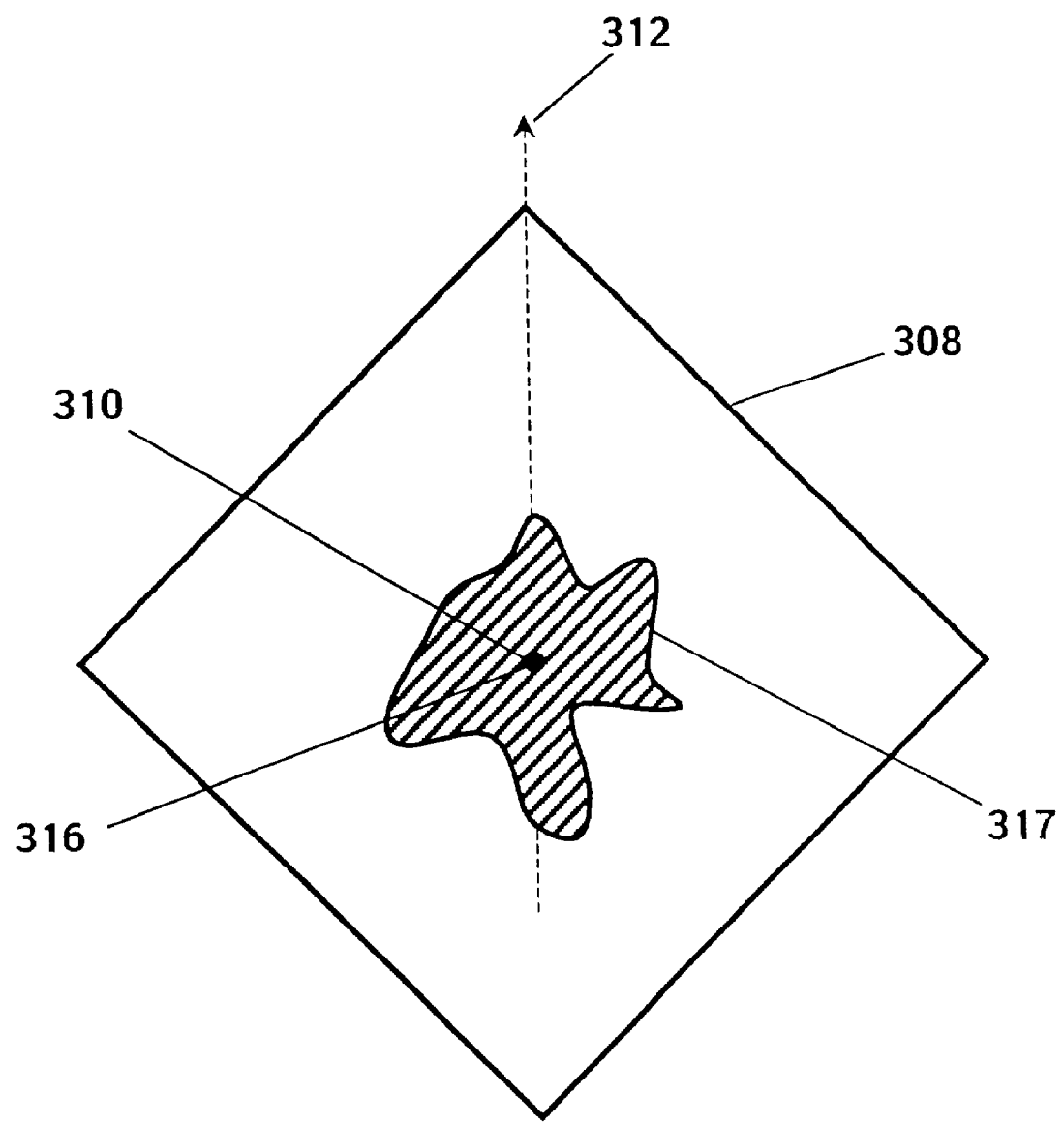
FIG. 13 is a schematic illustration of a front view of an image plane.

FIG. 13 shows a front view of the image plane 308 corresponding to the imaging setup shown in FIG. 12. The drawing of the image plane 308 in FIG. 13 is made from the point of view where the positive direction of the optic axis 310 is pointing into the page, away from the reader. Note that the "up" direction is defined as pointing up on the page, as denoted by the y-axis 312 shown in FIG. 13. An example of an image 317 is shown formed on the image plane 308. In this case, the image 317 is formed such that it is centered on the optic axis 310. Note that the on-axis image point 316 is shown as substantially coincident with the intersection of the imaging plane 308 and the optic axis 310.

Figure 14:
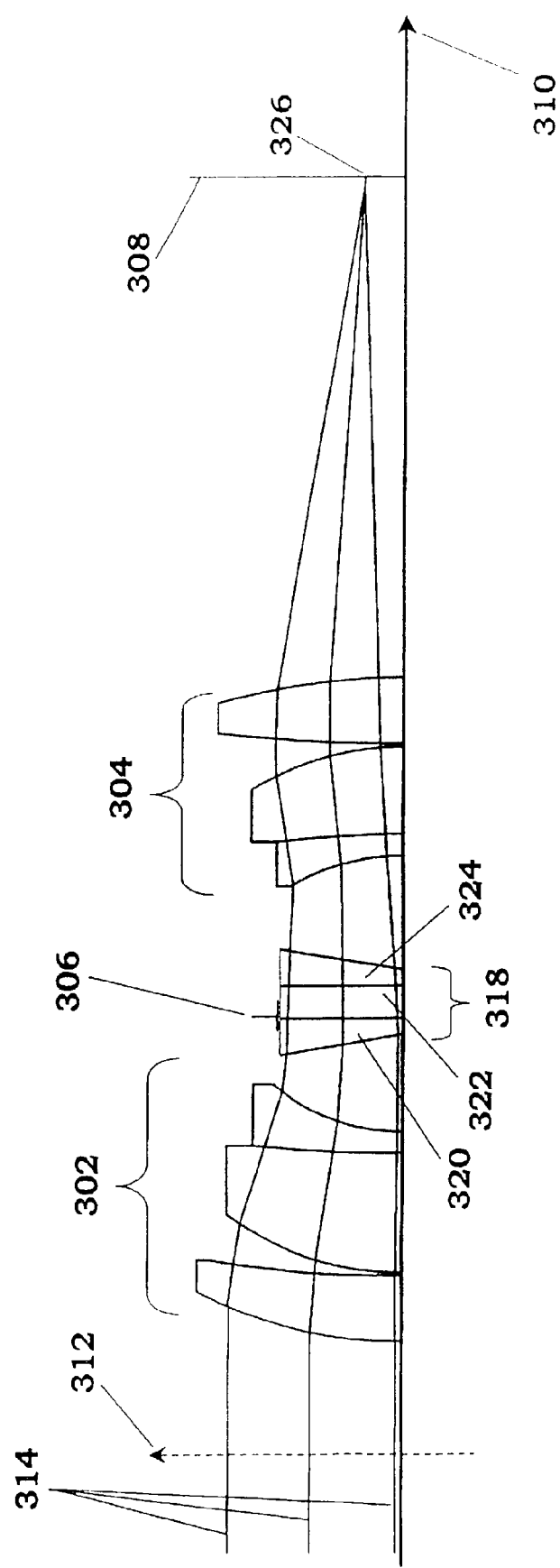
FIG. 14 is a schematic illustration of a cutaway side view of the top portion of an imaging lens system with a prism and filter group inserted at the aperture stop.

FIG. 14 shows a cutaway side view of the top portion of the same imaging system that was shown in FIG. 12, this time with a prism and filter group 318 inserted at a location substantially coincident with the aperture stop 306. The prism and filter group 318 comprises a first prism 320, a first filter plane 322, and a second prism 324. The first prism 322 and second prism 326 act together to bend the light rays 314 in such a way that they come to focus at a point 326 on the image plane 308, which point is moved away from the optic axis 310.

Figure 15:
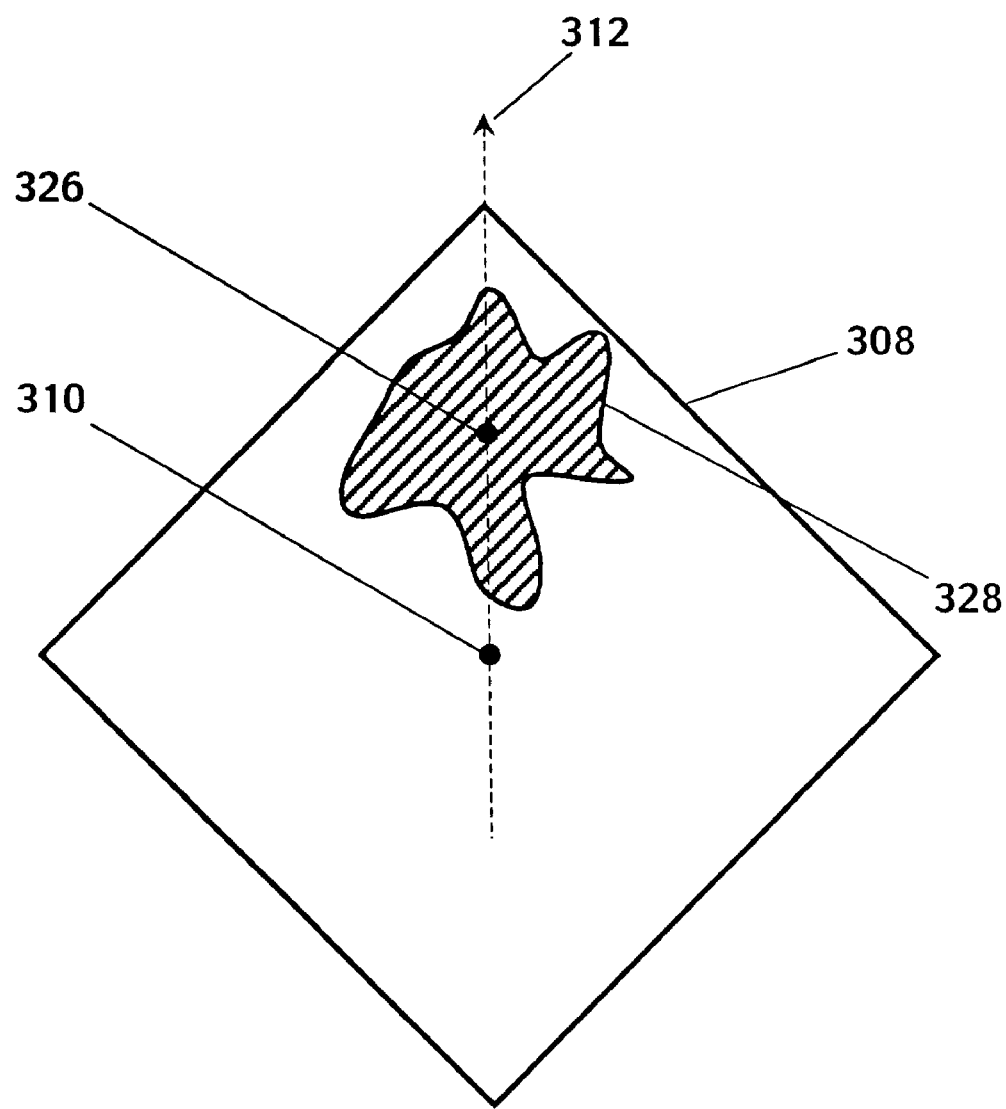
FIG. 15 is a schematic illustration of a front view of another image plane.

FIG. 15 shows a front view of the image plane 308 corresponding to the imaging setup shown in FIG. 14. The drawing of the image plane 308 in FIG. 15 is made from the point of view where the positive direction of the optic axis 310 is pointing into the page, away from the reader. Note that the "up" direction is defined as pointing up on the page, as denoted by the y-axis 312 shown in FIG. 15. An example of an image 328 is shown formed on the image plane 308. In this case, the image 328 is formed such that it is centered at a point well removed from the optic axis 310. Note that the on-axis image point 326 is shown as a point well removed from the optic axis 310. Note that the insertion of the prism and filter group 318, as shown in FIG. 14, is the reason for the change in position of the image 328 and the on-axis image point 326 on the image plane 308.

The filter and prism group 318 shown in FIG. 14 is one of many possible embodiments of a filter and prism group that could effect the movement of the image 328 as demonstrated above.

FIG. 16a shows another embodiment for the filter and prism group 330, as it might be inserted into the system shown in FIG. 12, at a location substantially coincident with the aperture stop 306. Note that in FIG. 16a, the optic axis 310 is shown and that the positive direction is toward the right on the page. Note also that the "up" direction is defined as pointing up on the page, as denoted by the y-axis 312 shown in FIG. 16a. In FIG. 16a, the filter and prism group 330 comprises a first prism 332, a filter 334, and a second prism 336, none of which elements are touching one another.

FIG. 16b shows yet another embodiment for the filter and prism group 338, as it might be inserted into the system shown in FIG. 12, at a location substantially coincident with the aperture stop 306. Note that in FIG. 16b, the optic axis 310 is shown and that the positive direction is toward the right on the page. Note also that the "up" direction is defined as pointing up on the page, as denoted by the y-axis 312 shown in FIG. 16b. In FIG. 16b, the filter and-prism group 338 comprises one prism 340 and a filter 342. The prism 340 filter 342 are not in contact with each other in this FIG. 16c shows still yet another embodiment for the filter and prism group 344, as it might be inserted into the system shown in FIG. 12, at a location substantially coincident with the aperture stop 306. Note that in FIG. 16c, the optic axis 310 is shown and that the positive direction is toward the right on the page. Note also that the "up" direction is defined as pointing up on the page, as denoted by the y-axis 312 shown in FIG. 16c. In FIG. 16c, the filter and prism group 344 comprises a first prism 346, a filter 348, and a second prism 350. Note that in this case the first prism 346 and the filter 348 are in contact with one another. Note also that the angle of the first prism 346 is different than the angle of the second prism 350.

It should be noted that there are numerous possible configurations for the filter and prism group that are within the scope of the invention.

Figure 17:
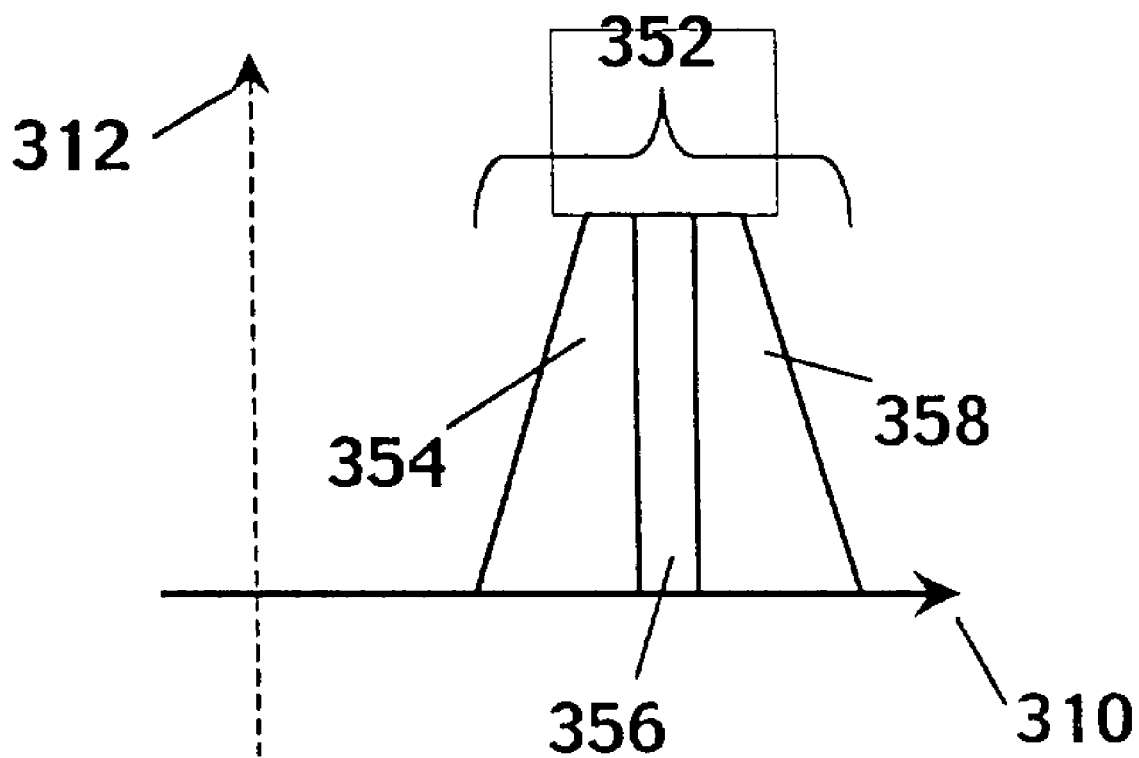
FIG. 17 is a schematic illustration of yet another form for the filter and prism group.

FIG. 17 shows yet another form for the filter and prism group 352, as it might be inserted into the system shown in FIG. 12, at a location substantially coincident with the aperture stop 306. Note that in FIG. 17, the optic axis 310 is shown and that the positive direction is toward the right on the page. Note also that the "up" direction is defined as pointing up on the page, as denoted by the y-axis 312 shown in FIG. 17. In FIG. 17, the filter and prism group 352 comprises a first prism 354, a filter 356, and a second prism 358. Note that in this case the direction of angles on the first prism 354 and the second prism 358 are opposite the directions of angles of the prisms shown in FIG. 14, FIG. 16a, FIG. 16b, and FIG. 16c. The effect of inserting this filter and prism group 352 into an optical system like the one shown in FIG. 12 is shown in FIG. 18.

Figure 18:
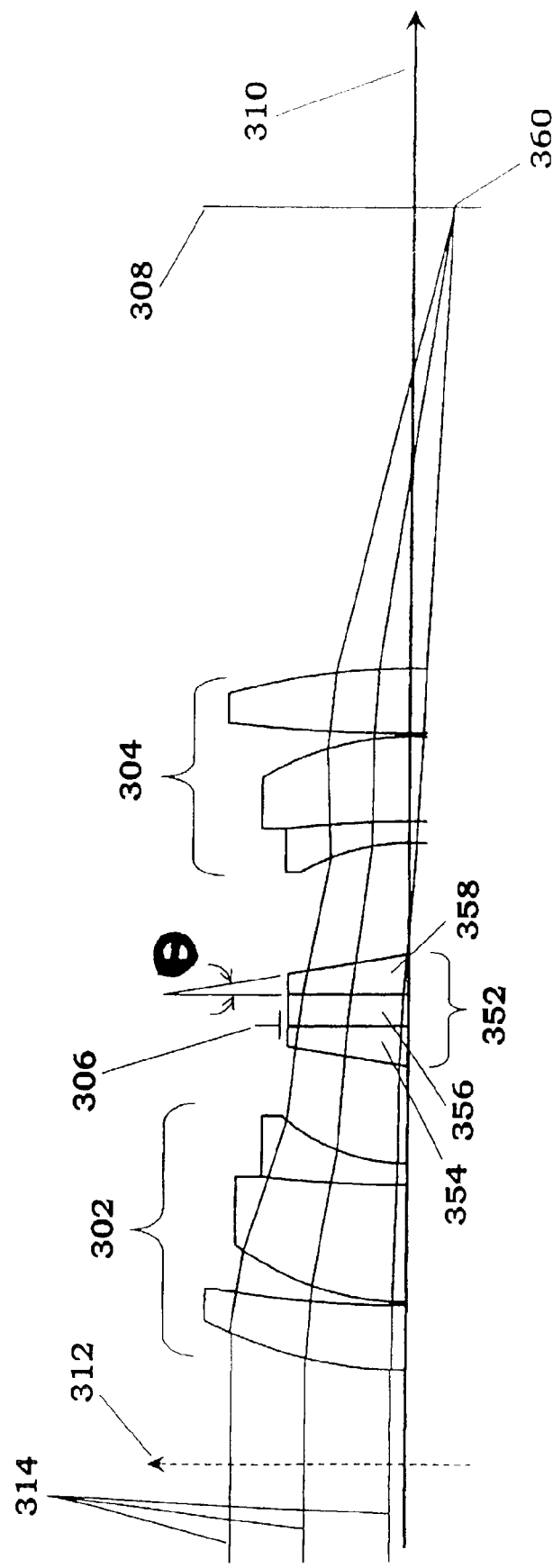
FIG. 18 is a schematic illustration of a cutaway side view of the top portion of an imaging lens system with another prism and filter group inserted at the aperture stop.

FIG. 18 shows a cutaway side view of a portion of the same imaging system that was shown in FIG. 12, this time with a prism and filter group 352 inserted at a location substantially coincident with the aperture stop 306. The prism and filter group 352 comprises a first prism 354, a first filter plane 356, and a second prism 358. Note that the angle of the second prism 358 is labeled as θ in FIG. 18. The first prism 354 and second prism 358 act together to bend the light rays 314 in such a way that they come to focus at a point 360 on the image plane 308, which point is moved away from the optic axis 310. Note that the on-axis focus point 360 is moved down away from the optic axis 310, whereas the insertion of an oppositely-angled filter and prism group 318 previously caused the on-axis image point 326 to move up away from the optic axis 310 as shown previously in FIG. 14.

Figure 19:
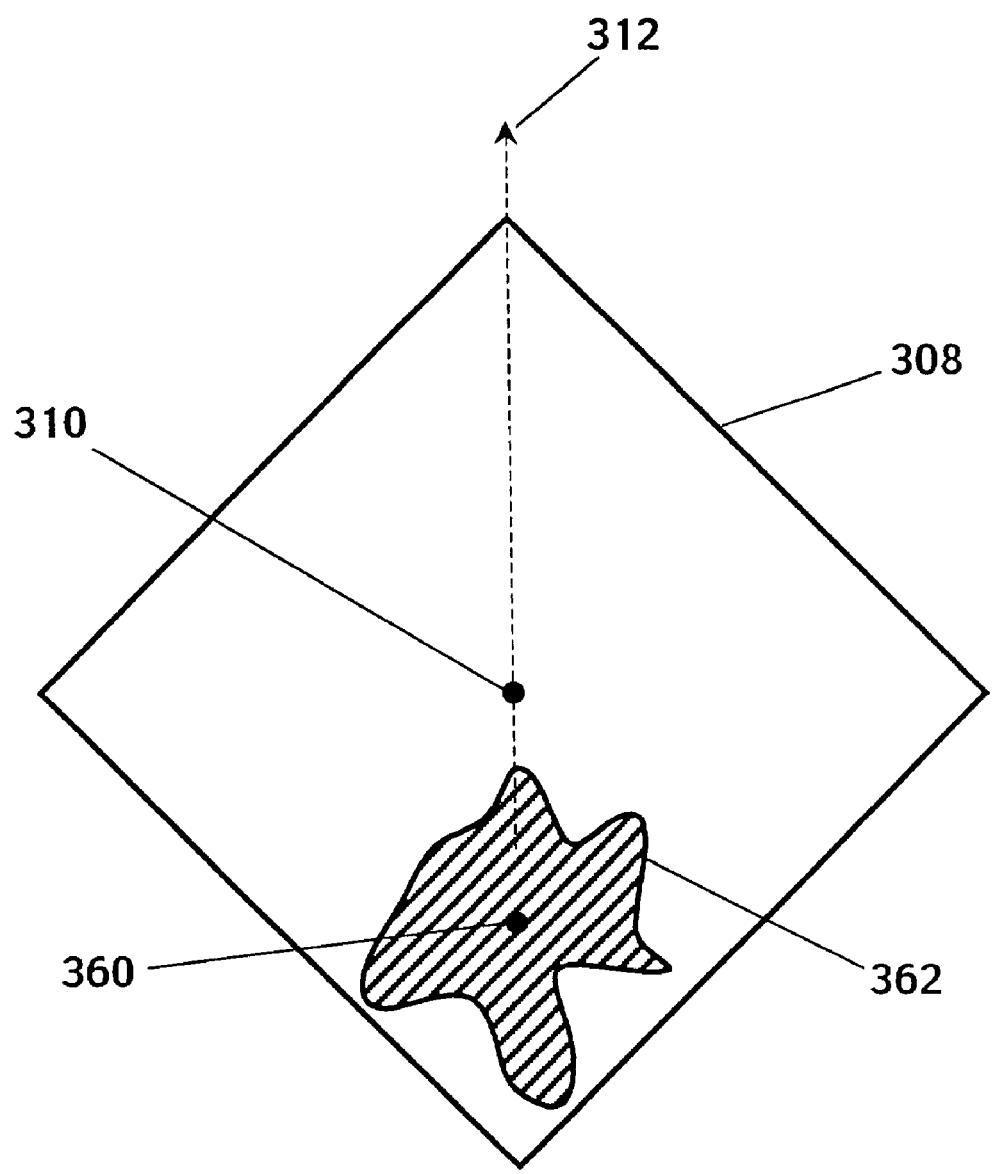
FIG. 19 is a schematic illustration of a front view of yet another image plane.

FIG. 19 shows a front view of the image plane 308 corresponding to the imaging setup shown in FIG. 18. The drawing of the image plane 308 in FIG. 19 is made from the point of view where the positive direction of the optic axis 310 is pointing into the page, away from the reader. Note that the "up" direction is defined as pointing up on the page, as denoted by the y-axis 312 shown in FIG. 19. An example of an image 362 is shown formed on the image plane 308. In this case, the image 362 is formed such that it is centered at a point well removed from the optic axis 310. Note that the on-axis image point 360 is shown as a point well removed from the optic axis 310. Note that the insertion of the prism and filter group 352, as shown in FIG. 18, is the reason for the change in position of the image 362 and the on-axis image point 360 on the image plane 308. Note also that because the angles of the faces on the prisms 354 and 358 (as shown in FIG. 18) are opposite the angles of the faces on the prisms 320 and 324 (as shown in FIG. 14), the direction of movement of the image 317 and on-axis image point 316 is also opposite.

The filter and prism group 352 shown in FIG. 18 is one of many possible embodiments of a filter and prism group that could effect the movement of the image 362 as demonstrated above.

FIG. 20a shows another form for the filter and prism group 364, as it might be inserted into the system shown in FIG. 12, at a location substantially coincident with the aperture stop 306. Note that in FIG. 20a, the optic axis 310 is shown and that the positive direction is toward the right on the page. Note also that the "up" direction is defined as pointing up on the page, as denoted by the y-axis 312 shown in FIG. 20a. In FIG. 20a, the filter and prism group 364 comprises a first prism 366, a filter 368, and a second prism 370, none of which elements are touching one another.

FIG. 20b shows yet another form for the filter and prism group 372, as it might be inserted into the system shown in FIG. 12, at a location substantially coincident with the aperture stop 306. Note that in FIG. 20b, the optic axis 310 is shown and that the positive direction is toward the right on the page. Note also that the "up" direction is defined as pointing up on the page, as denoted by the y-axis 312 shown in FIG. 20b. In FIG. 20b, the filter and prism group 372 comprises one prism 374 and a filter 376. The prism 374 and filter 376 are not in contact with each other in this case.

FIG. 20c shows yet another embodiment for the filter and prism group 378, as it might be inserted into the system shown in FIG. 12, at a location substantially coincident with the aperture stop 306. Note that in FIG. 20c, the optic axis 310 is shown and that the positive direction is toward the right on the page. Note also that the "up" direction is defined as pointing up on the page, as denoted by the y-axis 312 shown in FIG. 20c. In FIG. 20c, the filter and prism group 378 comprises a first prism 380, a filter 382, and a second prism 384. Note that in this case the first prism 380 and the filter 382 are in contact with one another. Note also that the angle of the first prism 380 is different than the angle of the second prism 384.

It should be noted that there are numerous possible configurations for the filter and prism group that are within the scope of the invention.

It should also be noted that movement of the images 317, 328, 362 in the image plane 308 occurs in the plane of the slope angle θ of the prism or prisms used in the filter and prism groups 318, 352. It should also be noted that the amount of movement of the images 317, 328, 362 in the image plane 308 is proportional to the size of the slope angle θ of the prism or prisms used in the filter and prism groups 318, 352. Thus, if more movement of the image 328, 362 is desired, then a larger slope angle θ of the prisms 320, 324, 354, 358 would be called for.

Figure 21B:
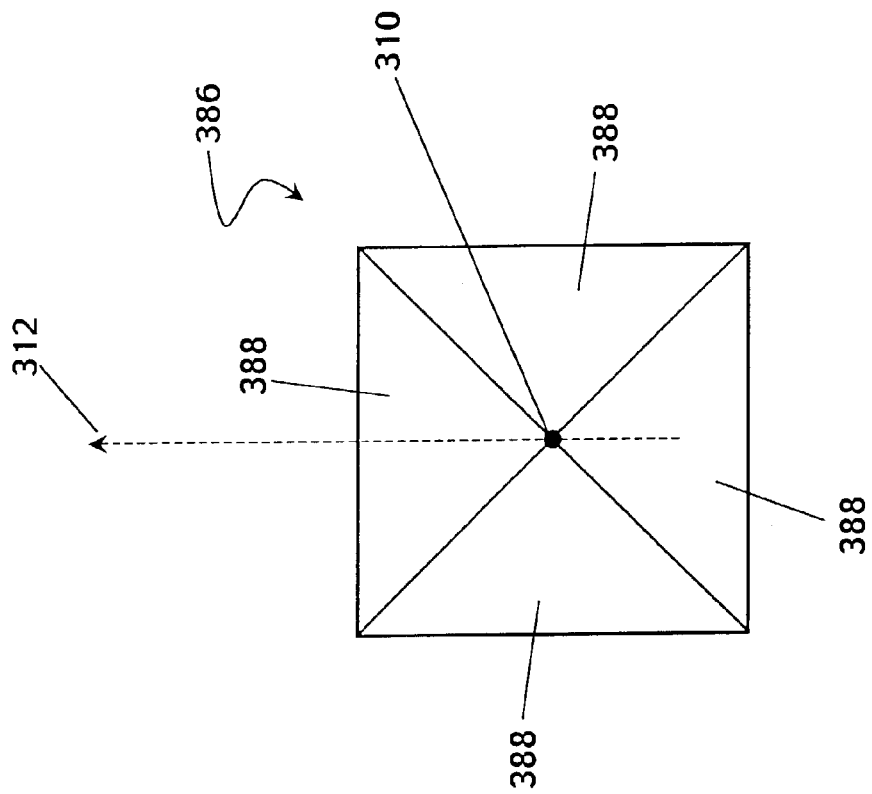
FIG. 21b is a schematic illustration of a front-view of a multiple-faceted prism with four facets.
Figure 21A:
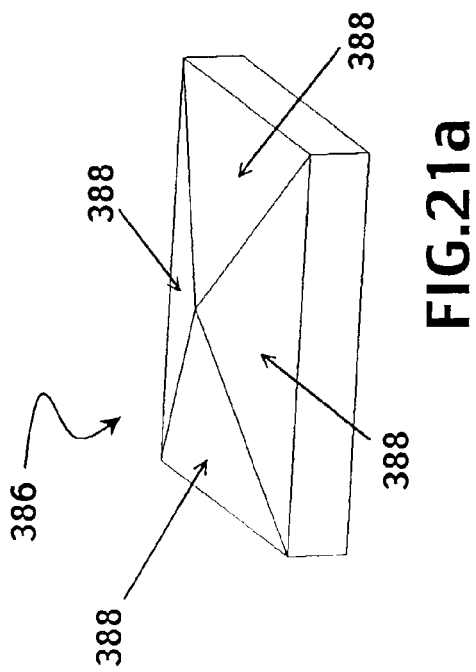
FIG. 21a is a schematic illustration of a perspective view of a multiple-faceted prism with four facets.
Figure 21C:
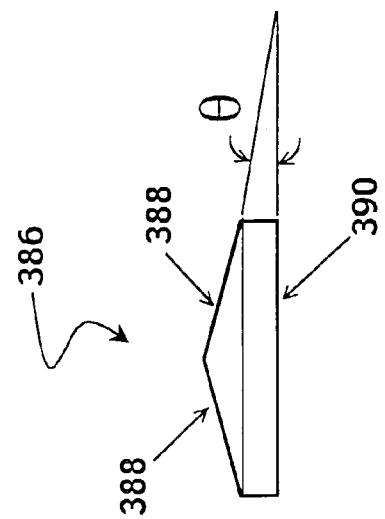
FIG. 21c is a schematic illustration of a side-view of a multiple-faceted prism with four facets.

By using multiple-faceted prisms, it is possible to create multiple images in the image plane. FIG. 21a shows a perspective drawing of what such a multiple-faceted prism 386 would look like with four facets 388. FIG. 21b shows a front view of what such a multiple-faceted prism 386 would look like with four facets 388. FIG. 21c shows a side view of what such a multiple-faceted prism 386 would look like with four facets 388. Note that each of the facets 388 comprises a flat plane that is not parallel to the back face 390 of the prism 386. Instead, each facet 388 forms an angle θ with respect to the back face 390 of the prism 386.

Figure 22:
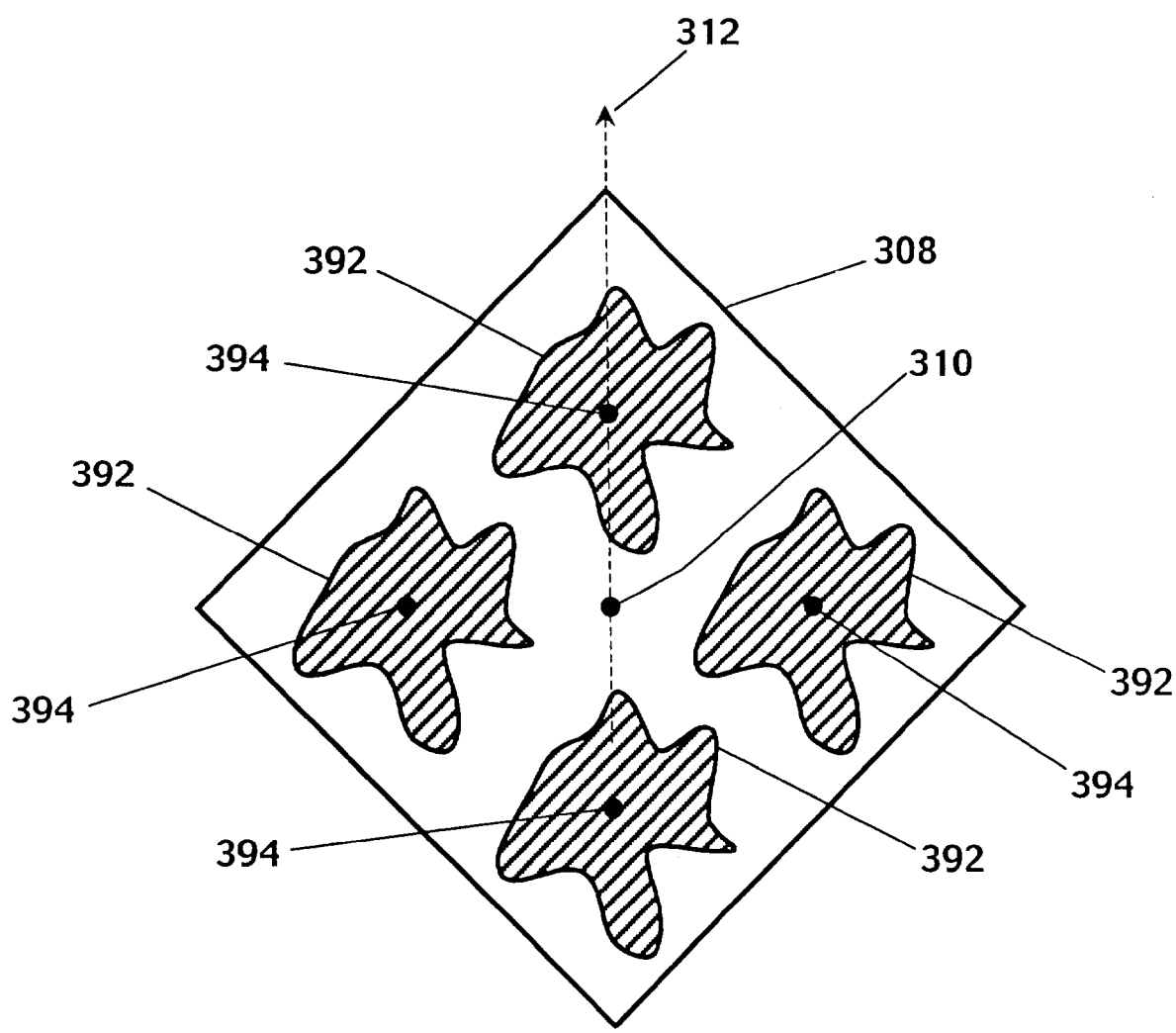
FIG. 22 is a schematic illustration of four images being formed simultaneously on a single image plane.

FIG. 22 shows an example of the image formation that would occur at the imaging plane 308 if a 4-faceted prism 386 were placed at a location substantially coincident with the aperture stop 306 of an imaging system 300 like the one shown in FIG. 11. Note that four identical copies of the same image 392 are formed on the image plane 308, at locations centered on the four on-axis image points 394. Each of these identical images 392 is formed by light that has passed through one of the facets 388 on the prism 386. Note that the location on the image plane 308 of each of the four on-axis image points 394 is controlled by the angle θ of each of the facets 388 on the prism 386.

Figure 23:
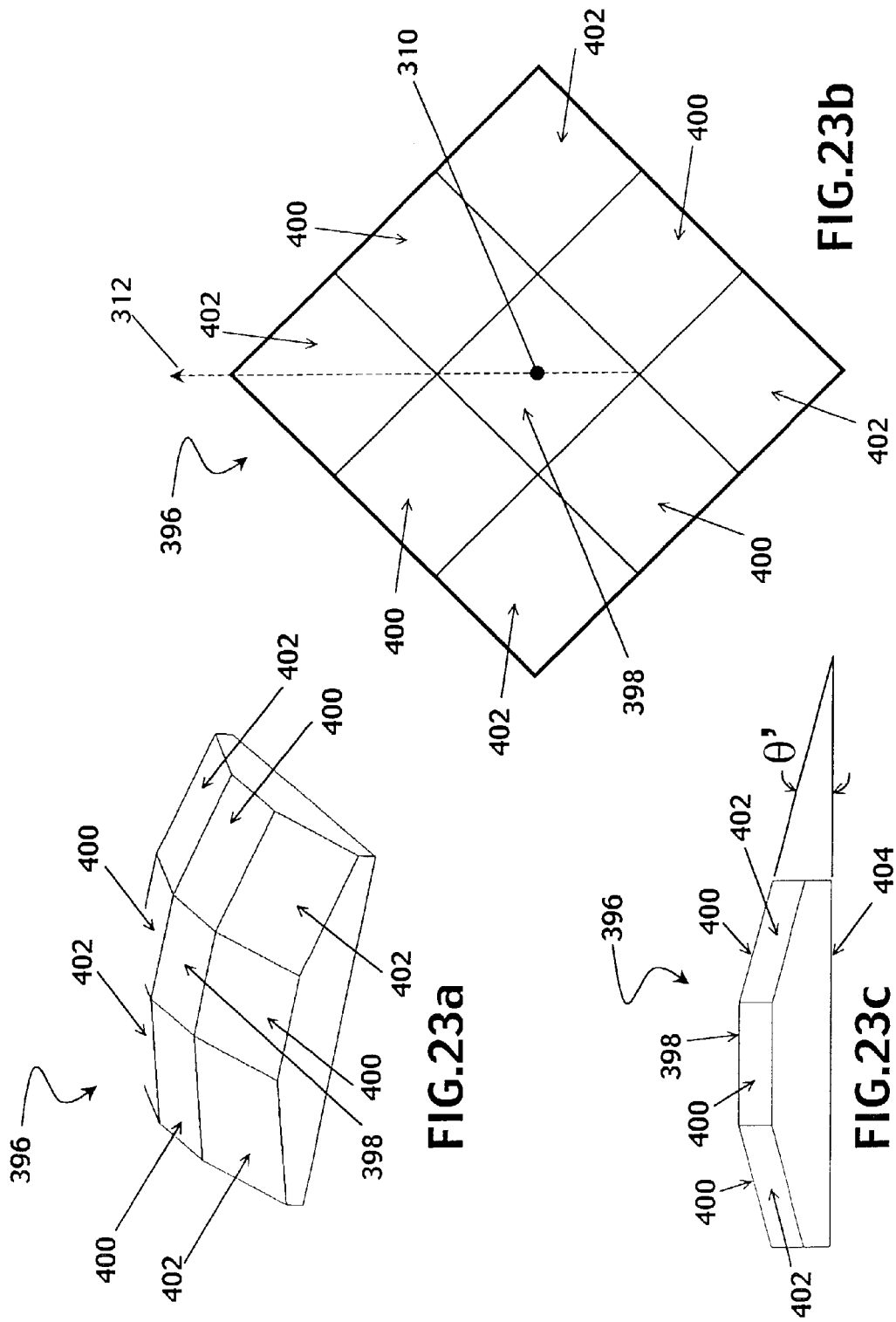
FIG. 23a is a schematic illustration of a perspective view of a multiple-faceted prism with nine facets.
FIG. 23b is a schematic illustration of a front-view of a multiple-faceted prism with nine facets.
FIG. 23c is a schematic illustration of a side-view of a multiple-faceted prism with nine facets.

FIG. 23a shows a perspective drawing of what a multiple-faceted prism 396 would look like with nine facets 398, 400, 402. FIG. 23b shows a front view of what such a multiple-faceted prism 396 would look like with nine facets 398, 400, 402. FIG. 23c shows a side view of what such a multiple-faceted prism 386 would look like with nine facets 398, 400, 402. Note that each of the facets 398, 400, 402 comprises a flat plane that is not parallel to the back face 404 of the prism 396. Note that the facets 398, 400, 402 of the prism 396 make different angles with respect to the back face 404 of the prism 396, wherein the angles of the facets 398, 400, 402 depend on the placement of the facets 398, 400, 402. For example the center facet 398 is parallel to the back face 404 of the prism 396. The four edge facets 400 form an angle θ' with the back face 404 of the prism 396. The four corner facets 402 form an angle with the back face 404 of the prism 396 that is larger than θ'.

Figure 24:
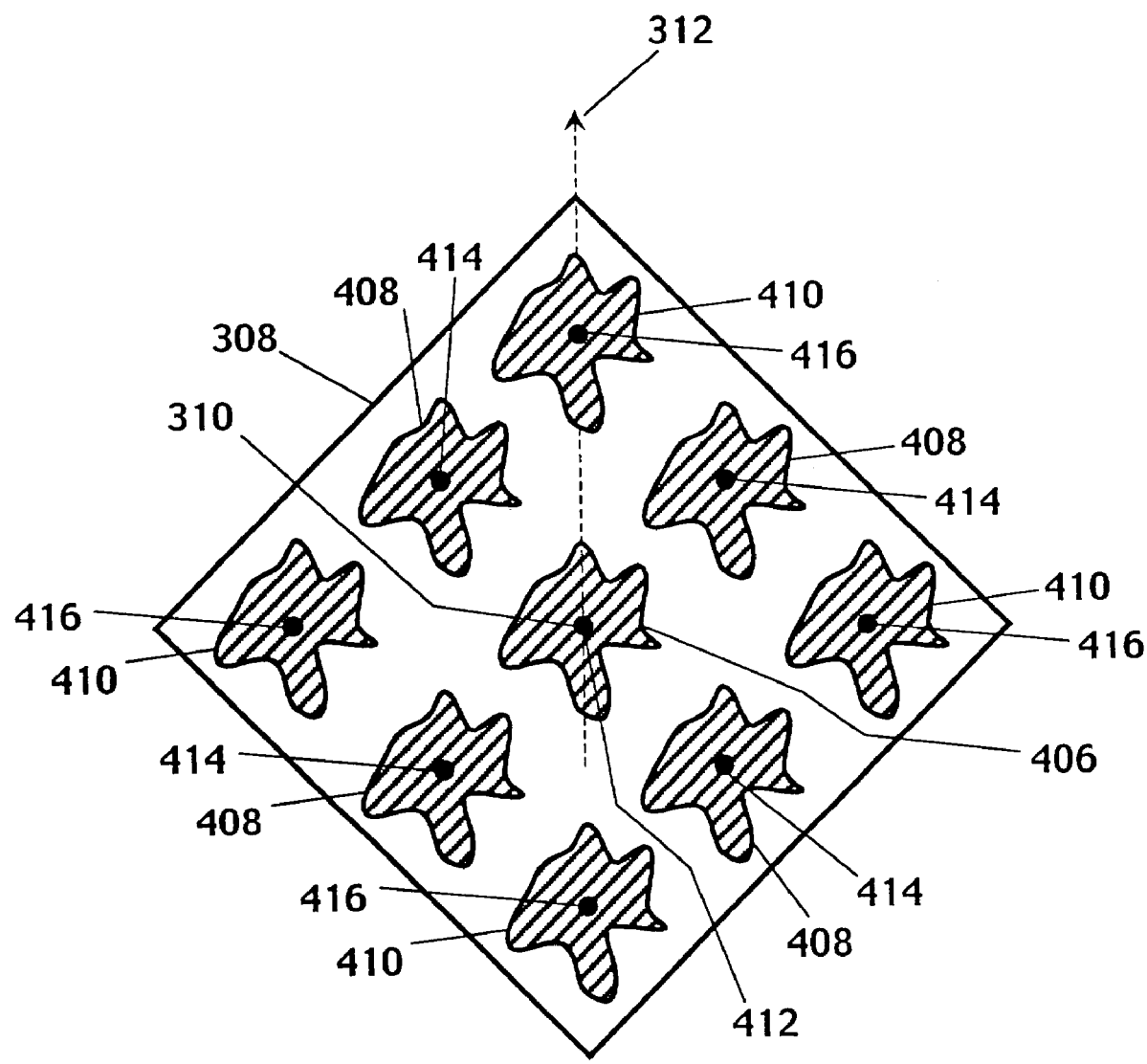
FIG. 24 is a schematic illustration of nine images being formed simultaneously on a single image plane.

FIG. 24 shows an example of the image formation that would occur at the imaging plane 308 if a 9-faceted prism 396 were placed at a location substantially coincident with the aperture stop 306 of an imaging system 300 like the one shown in FIG. 11. Note that nine identical copies of the same image 406, 408, 410 are formed on the image plane 308, at locations centered on the nine on-axis image points 412, 414, 416. Each of these identical images 406, 408, 410 is formed by light that has passed through one of the facets 398, 400, 402 on the prism 396. Note that the location on the image plane 308 of each of the nine on-axis image points 412, 414, 416 is controlled by the angle of each of the facets 398, 400, 402 on the prism 396. Thus, the center image 406 is centered on the center on-axis image point 412, which on-axis image point 412 is coincident with the intersection of the optic axis 310 and the image plane 308. The center image 406 is formed by light that has passed through the center facet 398 of the prism 396 as shown in FIG. 23a, FIG. 23b, FIG. 23c. Likewise, the edge images 408 are centered on the edge on-axis image points 414. The edge images 408 are formed by light that has passed through the edge facets 400 of the prism 396 as shown in FIG. 23a, FIG. 23b, FIG. 23c. Similarly, the corner images 410 are centered on the corner on-axis image points 416. The corner images 410 are formed by light that has passed through the corner facets 402 of the prism 396 as shown in FIG. 23a, FIG. 23b, FIG. 23c.

Referring to FIG. 22 and FIG. 24 it can be seen that if each of the images 392, 406, 408, 410 is large, then light from the multiple images 392, 406, 408, 410 will overlap on the image plane 308. Because this is a typically undesirable effect, it is important to prevent light from any one of the images 392, 406, 408, 410 from becoming incident on the part of the image plane 308 corresponding to any other of the images 392, 406, 408, 410. The method for achieving this goal is through the process of matching filters. The process for matching filters is explained below.

Figure 25:
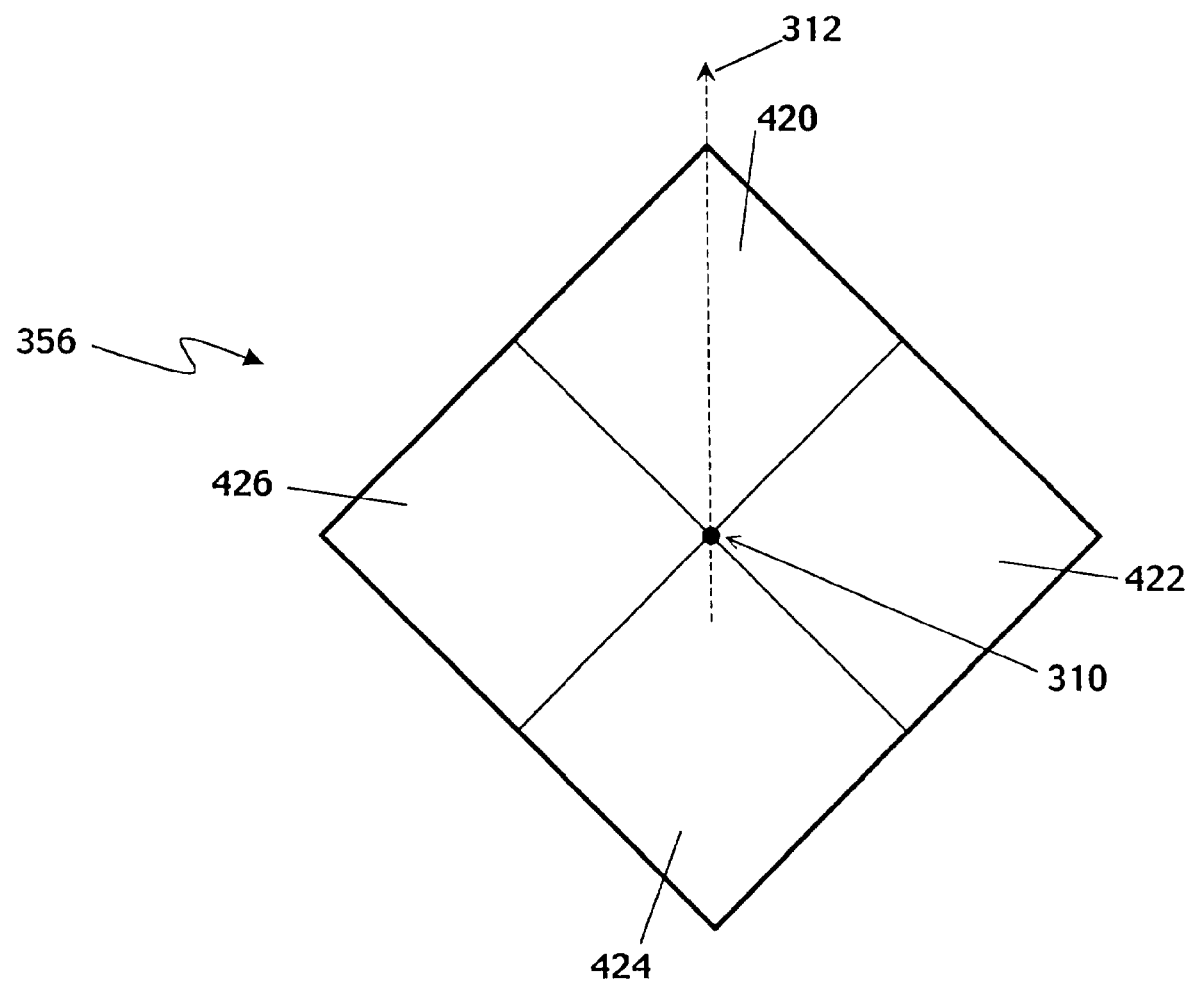
FIG. 25 is a schematic illustration of a front-view of a 4-part filter.

The process for matching filters involves first choosing a filter for the filter and prism group 352 as shown in FIG. 18. For example, let us examine the case where the prisms 354, 358 in the filter and prism group 352 comprise 4-faceted prisms like the ones shown in FIG. 21a, FIG. 21b, FIG. 21c. In this case, the filter 356 in the filter and prism group 352 would comprise a 4-part filter 356 like the one shown in FIG. 25. Four individual filters 420, 422, 424, 426 comprise the 4-part filter 356 as shown in FIG. 25. Each filter 420, 422, 424, 426 in the 4-part filter 356 is chosen so as to transmit only a portion of the light, and furthermore each filter 420, 422, 424, 426 is chosen so as to transmit a portion of light that is not transmitted by any of the other filters 420, 422, 424, 426. In this way, each of the four filters 420, 422, 424, 426 is said to be exclusive of the other four filters 420, 422, 424, 426.

For the sake of clarity in this explanation, a specific example set of filters 420, 422, 424, 426 will be examined herein. However, it should be noted that there exists a practically infinite number of sets of exclusive filters 420, 422, 424, 426 that satisfy the scope of the present invention.

For example, the filter 420 in FIG. 25 might transmit only light with wavelengths between 425 nm and 450 nm. Also for example, the filter 422 in FIG. 25 might transmit only light with wavelengths between 500 nm and 525 nm. Also for example, the filter 424 in FIG. 25 might transmit only light with wavelengths between 575 nm and 600 nm. Also for example, the filter 426 in FIG. 25 might transmit only light with wavelengths between 650 nm and 675 nm.

Referring again to FIG. 18, it is apparent that the insertion of the filter and prism group 352 into the optical system as shown in FIG. 18 causes the on-axis image point to move to the opposite side of the optic axis 310 from the side of the axis that the prisms 354, 358 are on.

Figure 26:
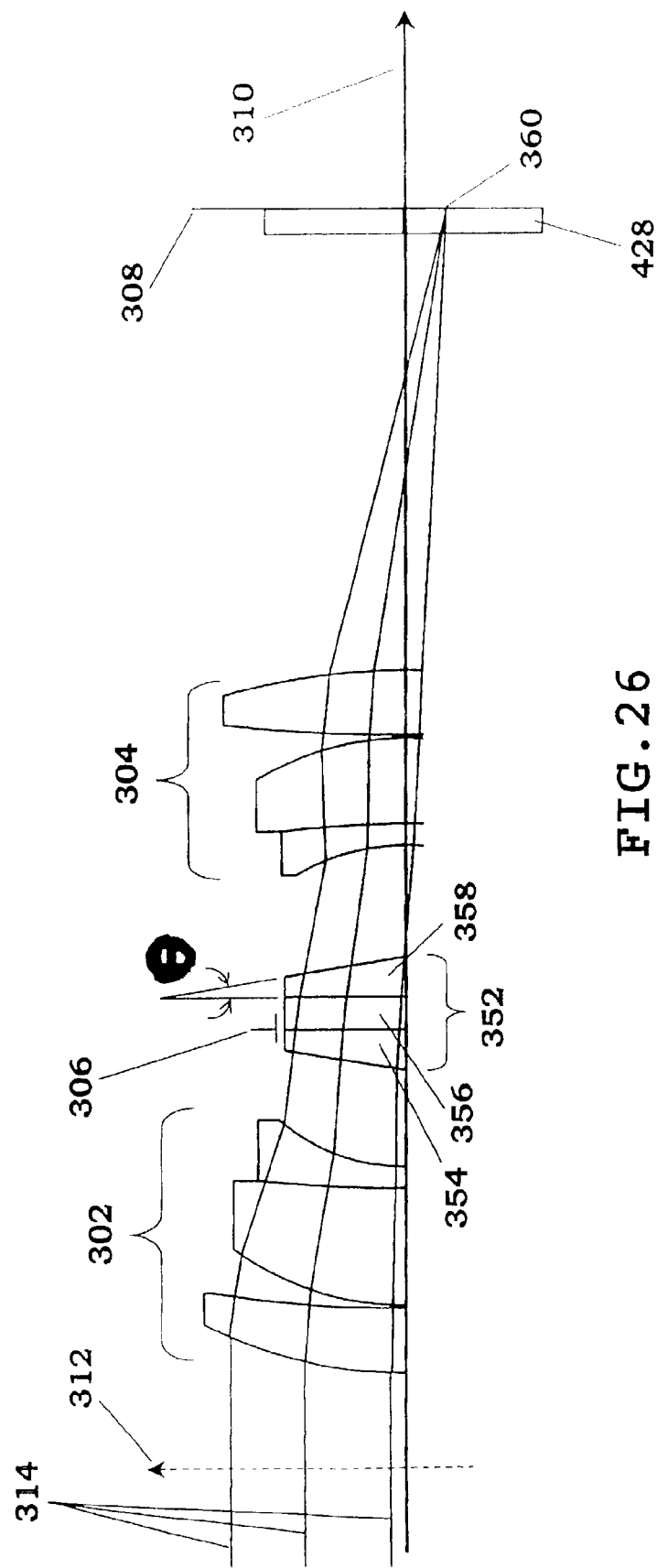
FIG. 26 is a schematic illustration of a cutaway side view of the top portion of an imaging lens system with a prism and filter group inserted at the aperture stop and a matching filter set inserted at the imaging plane; and, FIG. 27 is a schematic illustration of a front-view of a matching 4-part filter.

FIG. 26 shows the same optical imaging system shown in FIG. 18, this time with a second filter plane 428 inserted at a plane that is very near the image plane 308.

Figure 27:
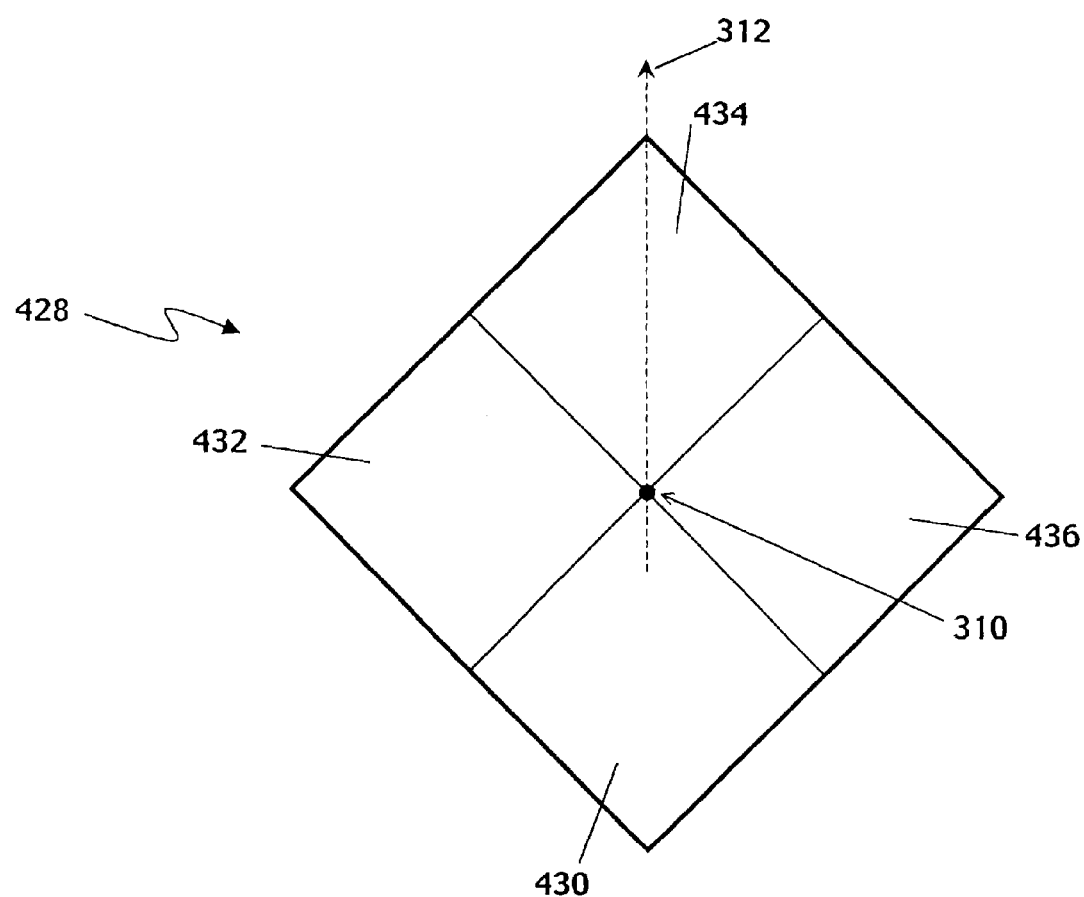

The second filter plane 428 comprises a 4-part filter 428 like the one shown in FIG. 27. Four individual filters 430, 432, 434, 436 comprise the 4-part filter 428 as shown in FIG. 27. Each filter 430, 432, 434, 436 in the 4-part filter 428 is chosen so as to transmit only a portion of the light, and furthermore each filter 430, 432, 434, 436 is chosen so as to transmit a portion of light that is transmitted by the corresponding filter 420, 422, 424, 426 in the first filter plane 356, and furthermore each filter 430, 432, 434, 436 is chosen so as to prevent transmission of a portion of light that is transmitted by the any of the other three non-corresponding filters 420, 422, 424, 426 in the first filter plane 356. In this way, each of the four filters 430, 432, 434, 436 in the second filter plane 428 is said to be matched to a specific one of the other four filters 420, 422, 424, 426 in the first filter plane 356.

For the sake of clarity in this explanation, a specific example set of filters 430, 432, 434, 436 will be examined herein. The example chosen below is meant to continue with the example set of filters 420, 422, 424, 426 outlined above. However, it should be noted that there exists a practically infinite number of sets of exclusive filters 430, 432, 434, 436 that satisfy the scope of the present invention.

For example, the filter 430 in FIG. 27 might transmit only light with wavelengths between 410 nm and 465 nm. Also for example, the filter 432 in FIG. 27 might transmit only light with wavelengths between 485 nm and 440 nm. Also for example, the filter 434 in FIG. 27 might transmit only light with wavelengths between 560 nm and 615 nm. Also for example, the filter 436 in FIG. 27 might transmit only light with wavelengths between 635 nm and 690 nm. Note that each filter 430, 432, 434, 436 in the second filter plane 428 is chosen so as to transmit only light that has been transmitted through the corresponding filter 420, 422, 424, 426 in the first filter plane 356, and to prevent transmission of light that has been transmitted through any of the three other non-corresponding filters 420, 422, 424, 426 in the first filter plane 356. Thus filter 430 in the second filter plane 428 corresponds to filter 420 in the first filter plane 356, and filter 432 in the second filter plane 428 corresponds to filter 422 in the first filter plane 356, and filter 434 in the second filter plane 428 corresponds to filter 424 in the first filter plane 356, and filter 436 in the second filter plane 428 corresponds to filter 426 in the first filter plane 356.

It should be noted that although embodiments of the present invention have been described in specific terms corresponding to a color corrected (chromatic aberration corrected) system for a pre-selected range of wavelengths, other embodiments are possible for different ranges of wavelengths. Embodiments are also possible where the filters in each of the filter planes transmit only certain polarization states or a combination of wavelength and polarization state or other radiation condition. Such embodiments would differ in specific components from the embodiments disclosed above.

Although the invention has been described with respect to a plurality of preferred embodiments, it should be realized this invention is also capable of a wide variety of further and other embodiments within the spirit and scope of the invention.

What is claimed is:

1. An optical system comprising:
   a first optical sub-system;
   a second optical sub-system;
   an aperture stop optically disposed between said first optical sub-system and said second optical sub-system;
   said first optical sub-system being capable of directing incoming electromagnetic radiation to a location of said aperture stop;
   a beam separating sub-system capable of receiving electromagnetic radiation from said first optical sub-system and separating received electromagnetic radiation into a plurality of beams of electromagnetic radiation, a location of said beam separating sub-system being substantially coincident with the location of said aperture stop; and
   said second optical sub-system being capable of imaging said plurality of beams of electromagnetic radiation received from said beam separating sub-system into a plurality of images on an image plane.

2. The optical system of claim 1 wherein said first optical sub-system, said second optical sub-system, and said beam separating subsystem are designed to substantially correct for chromatic aberrations.

3. The optical system of claim 1 further comprising:
   a filtering sub-system optically disposed between said second optical sub-system and the image plane.

4. An optical system comprising:
   a first optical sub-system;
   a second optical sub-system;
   an aperture stop optically disposed between said first optical sub-system and said second optical sub-system;
   said first optical sub-system being capable of directing incoming electromagnetic radiation to a location of said aperture stop;
   a beam separating sub-system capable of receiving electromagnetic radiation from said first optical sub-system and separating received electromagnetic radiation into a plurality of beams of electromagnetic radiation, a location of said beam separating sub-system being substantially coincident with the location of said aperture stop;
   said second optical sub-system being capable of imaging said plurality of beams of electromagnetic radiation received from said beam separating sub-system into a plurality of images on an image plane; and
   wherein the beam separating sub-system comprises at least one beam separating component and a mid-system filter system.

5. The optical system of claim 4 wherein said at least one beam-separating component comprises a plurality of optical elements, each of said elements comprising a facet oppositely located from a substantially flat facet, a normal to each said facet oppositely located from the substantially flat facet being at a preselected angle with respect to a predetermined optical axis.

6. The optical system of claim 5 wherein said plurality of facets comprises a composite convex surface.

7. The optical system of claim 5 wherein said plurality of facets comprises a composite concave surface.

8. The optical system of claim 5 wherein the beam separating sub-system further comprises:
   a first beam-separating component; and,
   a second beam-separating component;
   said mid-system filter system having a radiation receiving surface and a radiation emitting surface;
   said first beam-separating component being capable of receiving the electromagnetic radiation from said first optical sub-system and being capable of providing a plurality of beams of electromagnetic radiation to the radiation receiving surface of said mid-system filter system; and
   said second beam-separating component being capable of receiving radiation from the radiation emitting surface of said mid-system filter system.

9. The optical system of claim 8 wherein:
   each one of the substantially flat facets of said first beam-separating component is disposed on the radiation receiving surface of said mid-system filter system; and
   each one of the substantially flat facets of said second beam-separating component is disposed on the radiation emitting surface of said mid-system filter system.

10. The optical system of claim 8 wherein:
    each one of the substantially flat facets of said first beam-separating component is oppositely spaced apart from the radiation receiving surface of said mid-system filter system; and
    each one of the substantially flat facets of said second beam-separating component is oppositely spaced apart from the radiation emitting surface of said mid-system filter system.

11. The optical system of claim 8 wherein:
each one of the substantially flat facets of said first beam-separating component is disposed on the radiation receiving surface of said mid-system filter system; and
each one of the substantially flat facets of said second beam-separating component is oppositely spaced apart from the radiation emitting surface of said mid-system filter system.

12. The optical system of claim 5 wherein:
said at least one beam-separating component further comprises one beam separating component;
said mid-system filter system has a radiation receiving and a radiation emitting surface;
said first beam-separating component is capable of receiving the radiation from said first optical sub-system and is capable of providing a plurality of beams of electromagnetic radiation to the radiation receiving surface of said mid-system filter system.

13. The optical system of claim 12 wherein:
each one of the substantially flat facets of said one beam-separating component is oppositely spaced apart from the radiation receiving surface of said mid-system filter system.

14. The optical system of claim 4 wherein said at least one beam-separating component comprises a single optical element, said element comprising a plurality of facets, each of said facets from the plurality of facets being oppositely located from a single substantially flat facet, a normal to each of said facets from the plurality of facets being at a preselected angle with respect to a predetermined optical axis.

15. The optical system of claim 14 wherein said plurality of facets comprises a composite convex surface.

16. The optical system of claim 14 wherein said plurality of facets comprises a composite concave surface.

17. The optical system of claim 14 wherein the beam separating sub-system further comprises:
a first beam-separating component;
a second beam-separating component;
said mid-system filter system having a radiation receiving surface and a radiation emitting surface;
said first beam-separating component being capable of receiving the electromagnetic radiation from said first optical sub-system and being capable of providing a plurality of beams of electromagnetic radiation to the radiation receiving surface of said mid-system filter system; and,
said second beam-separating component being capable of receiving radiation from the radiation emitting surface of said mid-system filter system.

18. The optical system of claim 17 wherein: the substantially flat facet of said first beam-separating component is disposed on the radiation receiving surface of said mid-system filter system; and
the substantially flat facet of said second beam-separating component is disposed on the radiation emitting surface of said mid-system filter system.

19. The optical system of claim 17 wherein: the substantially flat facet of said first beam-separating component is oppositely spaced apart from the radiation receiving surface of said mid-system filter system; and
the substantially flat facet of said second beam-separating component is oppositely spaced apart from the radiation emitting surface of said mid-system filter system.

20. The optical system of claim 17 wherein: the substantially flat facet of said first beam-separating component is disposed on the radiation receiving surface of said mid-system filter system; and
the substantially flat facet of said second beam-separating component is oppositely spaced apart from the radiation emitting surface of said mid-system filter system.

21. The optical system of claim 14 wherein:
said at least one beam-separating component comprises one beam separating component;
said mid-system filter system has a radiation receiving and a radiation emitting surface;
said first beam-separating component is capable of receiving the radiation from said first optical sub-system and is capable of providing a plurality of beams of electromagnetic radiation to the radiation receiving surface of said mid-system filter system.

22. The optical system of claim 21 wherein:
the substantially flat facet of said one beam-separating component is oppositely spaced apart from the radiation receiving surface of said mid-system filter system.

23. The optical system of claim 4 wherein the mid-system filter system comprises a plurality of mid-system filters.

24. The optical system of claim 23 wherein said first optical sub-system, said second optical sub-system, and said beam separating subsystem are designed to substantially correct for chromatic aberrations.

25. The optical system of claim 24 wherein each one of said mid-system filters transmits radiation in a pre-selected band of wavelengths.

26. The optical system of claim 23 wherein each one of said mid-system filters transmits radiation of a pre-selected polarization.

27. The optical system of claim 23 further comprising: a filtering sub-system optically disposed between said second optical sub-system and the image plane.

28. The optical system of claim 27 wherein said filtering sub-system comprises an output filter system.

29. The optical system of claim 28 wherein the output filter system comprises a plurality of output filters, each of said output filters being substantially matched to a corresponding one of said mid-system filters.

30. The optical system of claim 29 wherein each of said output filters transmits radiation in a pre-selected band of wavelengths.

31. The optical system of claim 29 wherein each one of said mid-system filters transmits radiation of a pre-selected polarization.

32. A method for producing multiple images of a single object scene comprising the steps of:
delivering electromagnetic radiation from the single object scene to an aperture stop at a mid-plane;
providing a beam separating sub-system located substantially coincident with the aperture stop;
utilizing the beam separating sub-system to separate into a plurality of beams of electromagnetic radiation the electromagnetic radiation delivered to the mid-plane;
focusing the plurality of beams of electromagnetic radiation into a plurality of focused beams focused onto an imaging plane;
forming a plurality of images on the imaging plane from said plurality of focused beams.

33. The method of claim 32 further comprising the step of: filtering each one of said plurality of beams of electromagnetic radiation.

34. The method of claim 33 further comprising the step of: filtering each one of said plurality of focused beams.

* * * * *

UNITED STATES PATENT AND TRADEMARK OFFICE
CERTIFICATE OF CORRECTION

PATENT NO. : 7,177,085 B2  
APPLICATION NO. : 10/387851  
DATED : February 13, 2007  
INVENTOR(S) : Michael D. Tocci et al.

Page 1 of 1

It is certified that error appears in the above-identified patent and that said Letters Patent is hereby corrected as shown below:

On the title page, under (56) References Cited, Col. 1, line 3, under U.S. PATENT DOCUMENTS, add the following:

```
-- 5,414,458    5/1995   Harris et al. ...................348/92
   6,016,224    1/2000   Namiki .......................359/619
   6,031,619    2/2000   Wilkens et al. ............356/419
   6,222,631    4/2001   Terauchi ....................356/419
   6,304,330   10/2001   Millerd et al. .............356/521
   6,441,972    8/2002   Lesniak et al. ............359/741 --
```

On the title page, under (56) References Cited, Col. 2, line 2, under FOREIGN PATENT DOCUMENTS, add the following:

```
-- JP      09197263 A    7/1997
   WO      01/92940 A1  12/2001 --
```

Signed and Sealed this

Twenty-sixth Day of June, 2007

JON W. DUDAS  
*Director of the United States Patent and Trademark Office*